United States Patent
(12)
Ali et al.

(10) Patent No.: US 8,361,994 B2
(45) Date of Patent: Jan. 29, 2013

(54) PRIMARY AMINE DIAZENIUMDIOLATE HETEROCYCLIC DERIVATIVES

(75) Inventors: Amjad Ali, Freehold, NJ (US); Michael Man-Chu Lo, Edison, NJ (US); Zhiqiang Guo, Morganville, NJ (US); Brent Whitehead, Piscataway, NJ (US); Timothy J. Henderson, Edison, NJ (US); Lin Yan, East Brunswick, NJ (US); Shrenik K. Shah, Metuchen, NJ (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 0 days.

(21) Appl. No.: 13/412,032

(22) Filed: Mar. 5, 2012

(65) Prior Publication Data

US 2012/0232039 A1    Sep. 13, 2012

Related U.S. Application Data

(60) Provisional application No. 61/449,915, filed on Mar. 7, 2011, provisional application No. 61/525,254, filed on Aug. 19, 2011.

(51) Int. Cl.
| | |
|---|---|
| C07D 205/04 | (2006.01) |
| C07D 207/12 | (2006.01) |
| C07D 211/44 | (2006.01) |
| C07D 309/10 | (2006.01) |
| C07D 401/02 | (2006.01) |
| C07D 401/04 | (2006.01) |
| C07D 401/14 | (2006.01) |
| C07D 403/02 | (2006.01) |
| A61K 31/655 | (2006.01) |
| A61P 9/12 | (2006.01) |

(52) U.S. Cl. .................. 514/149; 534/551; 534/556
(58) Field of Classification Search .................. None
See application file for complete search history.

(56) References Cited

U.S. PATENT DOCUMENTS

| | | |
|---|---|---|
| 6,638,937 B2 | 10/2003 | Murugesan et al. |
| 6,852,745 B2 | 2/2005 | Murugesan et al. |
| 7,005,508 B2 | 2/2006 | Benedini et al. |
| 7,087,588 B2 | 8/2006 | Del Soldato |
| 7,186,753 B1 | 3/2007 | Del Soldato |
| 7,217,733 B2 | 5/2007 | Almirante et al. |
| 7,282,519 B2 | 10/2007 | Garvey et al. |
| 7,402,600 B2 | 7/2008 | Del Soldato |
| 7,834,042 B2 | 11/2010 | Sebhat et al. |
| 7,880,014 B2 | 2/2011 | Sebhat et al. |
| 7,947,664 B2 | 5/2011 | Ali et al. |
| 8,053,455 B2 | 11/2011 | Ali et al. |
| 8,106,034 B2 | 1/2012 | Ali et al. |
| 8,119,806 B2 | 2/2012 | Ali et al. |
| 2008/0194660 A1 | 8/2008 | Sebhat et al. |

FOREIGN PATENT DOCUMENTS

| | | |
|---|---|---|
| EP | 0 931 065 B1 | 7/2004 |
| WO | 92/01668 | 2/1992 |
| WO | 98/09948 | 3/1998 |
| WO | 2005/011646 | 2/2005 |
| WO | 2005/023182 | 3/2005 |
| WO | 2005/070868 | 8/2005 |
| WO | 2006/079610 | 8/2006 |
| WO | 2006/125016 | 11/2006 |
| WO | WO 2007000642 | 1/2007 |
| WO | WO 2007/144512 | 12/2007 |
| WO | 2009/004164 | 1/2009 |
| WO | 2009/070241 | 6/2009 |
| WO | WO2009/070241 | 6/2009 |
| WO | WO2009/094242 | 7/2009 |
| WO | WO2009/099853 | 8/2009 |
| WO | WO 2009/103875 A1 | 8/2009 |
| WO | WO2009/140111 | 11/2009 |
| WO | WO2010/014516 | 4/2010 |
| WO | WO2010/062415 | 6/2010 |
| WO | WO2010/065432 | 6/2010 |
| WO | WO2011/043914 | 4/2011 |
| WO | WO2011/053519 | 5/2011 |

OTHER PUBLICATIONS

Valdez, Carlos A. et al., "Hydrolytic Reactivity Trends among Potential Prodrugs of the O2-Glycosylated Diazeniumdiolate Family. Targeting Nitric Oxide to Macrophages for Antileishmanial Activity", Journal of Medicinal Chemistry, 51(13), 3961-3970, 2008.*
"New NO-Releasing Pharmacodynamic Hybrids of Losartan and Its Active Metabolite: Design, Synthesis, and Biopharmacological Properites", Maria C. Breschi, et al., J. Med. Chem. 2006, 49, 2628-2639.
Bohle, D., et al., "Primary amine diazeniumdiolate ions of structure {RNN(O)NOR'} as ambident nucleophiles", Tetrahedron Letters, vol. 50, No. 43, pp. 5917-5919, Oct. 28, 2009.
Saavedra, J., et al., "Chemistry of the Diazeniumdiolates. O- versus N-Alkylation of the RNH[N(O)NO] Ion", Journal of American Chemical Society, vol. 126, No. 40, pp. 12880-12887, 2004.

* cited by examiner

*Primary Examiner* — Fiona T Powers
(74) *Attorney, Agent, or Firm* — Richard S. Parr; Catherine D. Fitch

(57) ABSTRACT

A compound having the structure

I $$\underset{R^5}{\overset{R^1\ R^2}{\underset{R^6}{\diagdown\diagup}}}\!\!\!\!\!\!\!\!\!\underset{()_{1-4}}{\bigcirc}\!\!\!\!\!\!\!\!\!\!\!\!\underset{}{\text{O}}\!-\!\text{N}\!=\!\!\underset{\text{O}^-}{\overset{}{\text{N}^+}}\!-\text{NHR}^4$$

useful for treating hypertension, Pulmonary Arterial Hypertension (PAH), congestive heart failure, conditions resulting from excessive water retention, cardiovascular disease, diabetes, oxidative stress, endothelial dysfunction, cirrhosis, pre-eclampsia, osteoporosis or nephropathy.

32 Claims, No Drawings

PRIMARY AMINE DIAZENIUMDIOLATE HETEROCYCLIC DERIVATIVES

BACKGROUND OF THE INVENTION

WO09103875 describes diazeniumdiolate dihydro indole derivatives of a specified formula for treating hypertension and cardiovascular disease. WO07144512 describes diazeniumdiolate tetrazole-biphenyl derivatives of a specified formula for treating hypertension and cardiovascular disease. US 2005137191 describes nitrate ester compounds, e.g., 1,2-dichloro-4-(2-methyl-butyldisulfanyl)-benzene, useful for preventing or mitigating tissue and/or cellular damage associated with aging, septic shock, ulcers, gastritis, ulcerative colitis and Crohn's disease. US 2005065194 describes use of an endothelial gene differentiation receptor modulator such as 1-(2-ethoxyphenyl)-3-(hydroxyphenylamino)-pyrrolidine-2,5-dione, to modulate receptor-mediated biological activity such as cell proliferation stimulated by lysophosphatidic acid leading to ovarian cancer and other forms of cancer, and to treat conditions such as cancer, cardiovascular disease, ischemia, and atherosclerosis. WO 9746521 describes aliphatic nitrate esters useful for treating neurological conditions, especially Parkinson's, Alzheimer's and Huntington's disease.

The present invention relates to novel diazeniumdiolate heterocyclic derivatives, useful as antihypertensive agents.

SUMMARY OF THE INVENTION

The present invention includes diazeniumdiolate heterocyclic derivatives, including various pharmaceutically acceptable salts and hydrates of these forms, and pharmaceutical formulations comprising the diazeniumdiolate heterocyclic derivatives.

The invention also includes a method for treating hypertension, Pulmonary Arterial Hypertension (PAH), congestive heart failure, conditions resulting from excessive water retention, cardiovascular disease, diabetes, oxidative stress, endothelial dysfunction, cirrhosis, pre-eclampsia, osteoporosis or nephropathy, comprising administering a compounds of the invention to a patient having such a condition, or being at risk to having such condition.

DETAILED DESCRIPTION OF THE INVENTION AND PREFERRED EMBODIMENTS

The invention is a compound of formula I:

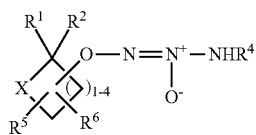

I or a pharmaceutically acceptable salt thereof, wherein
X is O or $NR^7$;

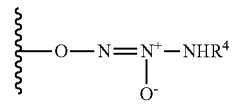

is attached to any ring carbon atom other than the carbon to which $R^1$ and $R^2$ are attached;
$R^1$ is hydrogen, —C(O)O$C_{1-6}$alkyl, or —C(O)OH, or together with $R^2$, forms =O;
$R^2$ is hydrogen, or together with $R^1$, forms =O;
$R^4$ is
— $C_{1-6}$alkyl,
— $CD_2C_{1-5}$alkyl,
— $C_{2-5}$alkylene-OH,
— $C_{2-5}$alkylene-O—C(O)$C_{1-6}$alkyl,
— $C_{1-6}$alkylene-aryl, or
— $CH_2CH$=$CH_2$;
$R^5$ and $R^6$, which are attached to any available carbon ring atom, are independently
hydrogen,
deuterium,
— $C_{1-6}$alkyl,
— C(O)O$C_{1-6}$alkyl,
— C(O)OH,
aryl,
or $R^5$ and $R^6$, when they are attached to the same carbon atom, together form =O;
$R^7$ is
hydrogen,
— $C_{1-6}$alkyl,
— $C_{1-6}$alkylene-aryl,
— $C_{1-6}$alkylene C(O)O—$C_{1-6}$alkyl,
— $C_{1-6}$alkylene-$CR^8R^9R^{10}$,
—CN,
—C(O)O—$C_{1-6}$alkyl,
—C(O)O—$C_{1-6}$alkylene $CR^8R^9R^{10}$,
—C(O)$C_{1-6}$alkyl,
—C(O)O$C_{3-6}$carbocycle,
—C(O)$CHF_2$,
—C(O)$CF_3$,
—C(O)$CH_2OH$,
—C(O)aryl,
—C(O)heteroaryl, wherein heteroaryl is an unsaturated 5- or 6-membered ring having 1-4 heteroatoms selected from N, O and S,
—C(O)$C_{1-6}$alkyleneOH,
—C(O)$C_{3-6}$carbocycle,
—C(O)$NH_2$,
—C(O)NH$C_{1-6}$alkyl,
—C(O)NH-adamantyl,
—C(O)heterocycle, wherein heterocycle is a saturated monocyclic 5- to 8-membered ring having 1-4 heteroatoms selected from N, O and S, or a 7- to 12-membered saturated bicyclic ring system having 1-6 heteroatoms selected from N, O and S,
—C(O)NH$C_{3-6}$carbocycle,
—C(O)N($C_{1-6}$alkyl)$C_{1-6}$alkyl,
—C(O)NH$SO_2$aryl,
—SO$C_{1-6}$alkyl,
—$SO_2C_{1-6}$alkyl,
—$SO_2$NH($C_{1-6}$alkyl),
—$SO_2$N($C_{1-6}$alkyl)($C_{1-6}$alkyl),
—$SO_2CF_3$,
—$SO_2$aryl,
—$SO_2$heteroaryl, wherein heteroaryl is an unsaturated 5- or 6-membered ring having 1-4 heteroatoms selected from N, O and S,
aryl,
an unsaturated 5- or 6-membered heteroaryl ring having 1-4 heteroatoms selected from N, O and S, or
—$C_{3-6}$carbocycle;

wherein aryl, alkyl, alkylene, carbocycle, heteroaryl, and heterocycle are unsubstituted or substituted with 1-4 groups independently selected from —CN, halogen, —CF$_3$, —OCF$_3$, —C(O)NH$_2$, —C$_{1-6}$alkyl, —C$_{3-6}$carbocycle, =O, —C(O)OC$_{1-6}$alky, —COOH, —C(CH$_3$)$_2$OH, —SO$_2$(C$_{1-6}$alkyl), aryl, an unsaturated 5-membered heteroaryl ring having 1-3 nitrogen atoms, or —OC$_{1-6}$alkyl, wherein R$^8$ and R$^9$, together with the carbon to which they are attached, form a C$_{3-6}$carbocycle or 4-8-membered heterocycle, and wherein R$^{10}$ is C$_{1-6}$alkyl;

and pharmaceutically acceptable salts thereof.

In one embodiment, the compound is of the formula which is

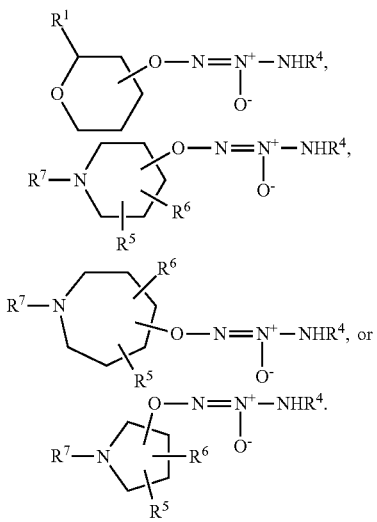

In another embodiment, the compound is of the formula which is

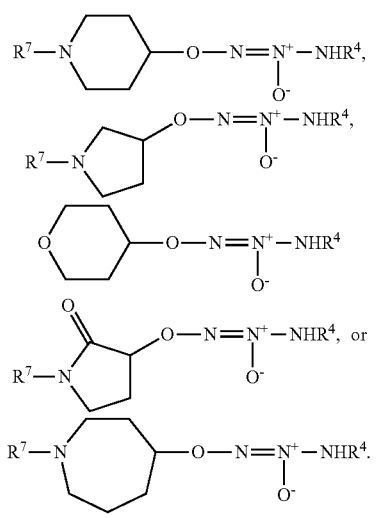

In another embodiment, the compound is of the formula which is

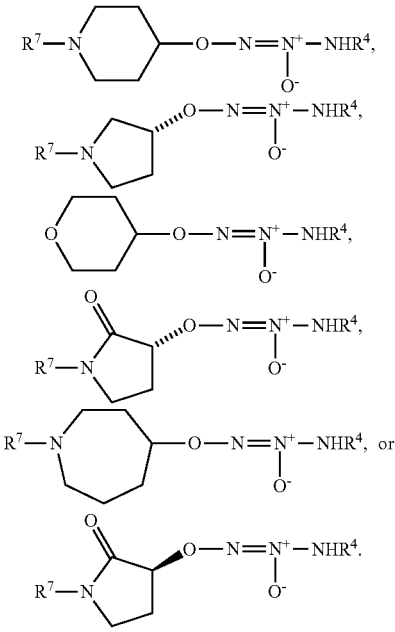

In another embodiment, R$^1$ is hydrogen.
In another embodiment, R$^2$ is hydrogen.
In another embodiment, X is —NR$^7$ and R$^7$.
—C$_{1-6}$alkyl,
—C$_{1-6}$alkylene-CR$^8$R$^9$R$^{10}$,
—C(O)O—C$_{1-6}$alkyl,
—C(O)O—C$_{1-6}$alkylene CR$^8$R$^9$R$^{10}$,
—C(O)C$_{1-6}$alkyl,
—C(O)OC$_{3-6}$carbocycle,
—C(O)CF$_3$,
—C(O)aryl,
—C(O)heteroaryl, wherein heteroaryl is an unsaturated 6-membered ring having 1-2 nitrogen atoms,
—C(O)NHC$_{1-6}$alkyl,
—C(O)NH-adamantyl,
—SO$_2$C$_{1-6}$alkyl,
aryl, or
heteroaryl, wherein heteroaryl is an unsaturated 6-membered ring having 1-2 nitrogen atoms,
wherein aryl, alkyl, alkylene, carbocycle, and heteroaryl are unsubstituted or substituted with 1-4 groups independently selected from —CN, —CF$_3$, Cl, —OCF$_3$, —C(O)NH$_2$, —C$_{1-6}$alkyl, —C$_{3-6}$carbocycle, =O, —C(O)OC$_{1-6}$alkyl, aryl, an unsaturated 5-membered heteroaryl ring having 3 nitrogen atoms or —OC$_{1-6}$alkyl, wherein R$^8$ and R$^9$, together with the carbon to which they are attached, form a C$_{3-6}$carbocycle or 4-8-membered heterocycle, and wherein R$^{10}$ is C$_{1-6}$alkyl.

In another embodiment, X is —NR$^7$ and R$^7$ is —C$_{1-6}$alkyl, wherein alkyl is unsubstituted or substituted with 1 or 2-CF$_3$.

In another embodiment, X is —NR$^7$ and R$^7$ is —C(O)O—C$_{1-6}$alkyl, —C(O)C$_{1-6}$alkyl, —C(O)O—C$_{1-6}$alkylene CR$^8$R$^9$R$^{10}$, —C(O)OC$_{3-6}$carbocycle, —C(O)CF$_3$, —C(O)aryl, —C(O)pyridyl, —C(O)NHC$_{1-6}$alkyl, or —C(O)NH-adamantyl, wherein alkyl is unsubstituted or substituted with aryl or —CF$_3$, wherein $R^8$ and $R^9$, together with the carbon to which they are attached, form a $C_{3-6}$carbocycle or 4-8-membered heterocycle, and
wherein $R^{10}$ is $C_{1-6}$alkyl.

In another embodiment, X is —$NR^7$ and $R^7$ is —$SO_2C_{1-6}$alkyl.

In another embodiment, X is —$NR^7$ and $R^7$ is aryl, wherein aryl is unsubstituted or substituted with 1-2 groups independently selected from —CN, —$CF_3$, —$OCF_3$, —$CH_3$ or an unsaturated 5-membered heteroaryl ring having 3 nitrogen atoms.

In another embodiment, X is —$NR^7$ and $R^7$ is an unsaturated heteroaryl 6-membered ring having 1-2 nitrogen atoms, wherein heteroaryl is unsubstituted or substituted with 1-4 groups independently selected from Cl, an unsaturated 5-membered heteroaryl ring having 3 nitrogen atoms, —CN, —$CF_3$, and —$C(O)NH_2$.

In a class of this embodiment, X is —$NR^7$ and $R^7$ is

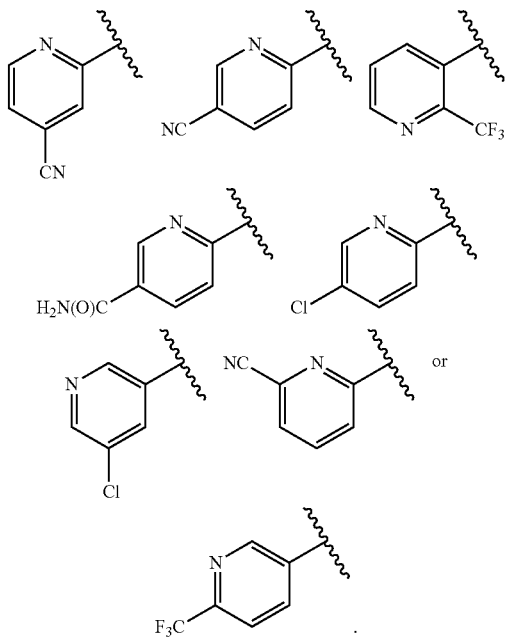

In another embodiment, $R^1$, $R^2$, $R^5$ and $R^6$ are hydrogen.

In another embodiment, $R^1$ and $R^2$, together with the atom to which they are attached, form =O, and $R^5$ and $R^6$ are hydrogen.

In another embodiment, $R^4$ is —$C_{1-6}$alkyl.
In another embodiment, $R^4$ is —$C(CH_3)_3$.
In another embodiment, X is —$NR^7$ and $R^7$ is
—$C_{1-6}$alkyl,
—$C_{1-6}$alkylene-aryl,
—$C_{1-6}$alkyleneC(O)O—$C_{1-6}$alkyl,
—$C_{1-6}$alkylene-$CR^8R^9R^{10}$,
—CN,
—C(O)O—$C_{1-6}$alkyl,
—C(O)O—$C_{1-6}$alkylene $CR^8R^9R^{10}$,
—C(O)$C_{1-6}$alkyl,
—C(O)O$C_{3-6}$carbocycle,
—C(O)$CHF_2$,
—C(O)$CF_3$,
—C(O)$CH_2OH$,
—C(O)aryl,
—C(O)heteroaryl, wherein heteroaryl is an unsaturated 5- or 6-membered ring having 1-4 heteroatoms selected from N, O and S,
—C(O)$C_{1-6}$alkyleneOH,
—C(O)$C_{3-6}$carbocycle,
—C(O)$NH_2$,
—C(O)NH$C_{1-6}$alkyl,
—C(O)NH-adamantyl,
—C(O)heterocycle, wherein heterocycle is a saturated monocyclic 5- to 8-membered ring having 1-4 heteroatoms selected from N, O and S, or a 7- to 12-membered saturated bicyclic ring system having 1-6 heteroatoms selected from N, O and S,
—C(O)NH$C_{3-6}$carbocycle,
—C(O)N($C_{1-6}$alkyl)$C_{1-6}$alkyl,
—C(O)NH$SO_2$aryl,
—SO$C_{1-6}$alkyl,
—$SO_2C_{1-6}$alkyl,
—$SO_2$NH($C_{1-6}$alkyl),
—$SO_2$N($C_{1-6}$alkyl)($C_{1-6}$alkyl),
—$SO_2CF_3$,
—$SO_2$aryl,
—$SO_2$heteroaryl, wherein heteroaryl is an unsaturated 5- or 6-membered ring having 1-4 heteroatoms selected from N, O and S,
aryl,
an unsaturated 5- or 6-membered heteroaryl ring having 1-4 heteroatoms selected from N, O and S, or
—$C_{3-6}$carbocycle;
wherein aryl, alkyl, alkylene, carbocycle, heteroaryl, and heterocycle are unsubstituted or substituted with 1-4 groups independently selected from —CN, halogen, —$CF_3$, —$OCF_3$, —$C(O)NH_2$, —$C_{1-6}$alkyl, —$C_{3-6}$carbocycle, =O, —C(O)O$C_{1-6}$alky, —COOH, —$C(CH_3)_2$OH, —$SO_2(C_{1-6}$alkyl), aryl, an unsaturated 5-membered heteroaryl ring having 1-3 nitrogen atoms, or —$OC_{1-6}$alkyl,
wherein $R^8$ and $R^9$, together with the carbon to which they are attached, form a $C_{3-6}$carbocycle or 4-8-membered heterocycle, and
wherein $R^{10}$ is $C_{1-6}$alkyl.

In another embodiment, compounds of the invention are
$O^2$-[1-(tert-butoxycarbonyl)piperidin-4-yl]1-(N-tert-butylamino)diazen-1-ium-1,2-diolate,
$O^2$-[(3R)-1-(tert-butoxycarbonyl)pyrrolidin-3-yl]1-(N-tert-butylamino)diazen-1-ium-1,2-diolate,
$O^2$-{(3R)-1-[(cyclohexyloxy)carbonyl]pyrrolidin-3-yl}1-(N-tert-butylamino)diazen-1-ium-1,2-diolate,
$O^2$-{(3R)-1-[(propan-2-yloxy)carbonyl]pyrrolidin-3-yl}1-(N-tert-butylamino)diazen-1-ium-1,2-diolate,
$O^2$-{(3R)-1-[(2,2-dimethylpropoxy)carbonyl]pyrrolidin-3-yl}1-(N-tert-butylamino)diazen-1-ium-1,2-diolate,
$O^2$-{(3R)-1-[(cyclopropylmethoxy)carbonyl]pyrrolidin-3-yl}1-(N-tert-butylamino)diazen-1-ium-1,2-diolate,
$O^2$-[(3R)-1-{[(3-methyloxetan-3-yl)methoxy]carbonyl}pyrrolidin-3-yl]1-(N-tert-butylamino)diazen-1-ium-1,2-diolate,
$O^2$-[(3R)-1-(2,2,2-trifluoroethyl)pyrrolidin-3-yl]1-(N-tert-butylamino)diazen-1-ium-1,2-diolate,
$O^2$-[(3R)-1-(tert-butylcarbamoyl)pyrrolidin-3-yl]1-(N-tert-butylamino)diazen-1-ium-1,2-diolate,
$O^2$-[(3R)-1-(tricyclo[3.3.1.13,7]dec-1-ylcarbamoyl)pyrrolidin-3-yl]1-(N-tert-butylamino)diazen-1-ium-1,2-diolate,
$O^2$-{(3R)-1-[2-phenylpropan-2-yl)carbamoyl]pyrrolidin-3-yl}1-(N-tert-butylamino)diazen-1-ium-1,2-diolate, O²-{(3R)-1-[(1,1,1-trifluoro-2-methylpropan-2-yl)carbamoyl]pyrrolidin-3-yl}1-(N-tert-butylamino)diazen-1-ium-1,2-diolate,
(±)—O²-[1-(tert-butylcarbamoyl)azepan-4-yl]1-(N-tert-butylamino)diazen-1-ium-1,2-diolate,
O²-(1-acetylpiperidin-4-yl)1-(N-tert-butylamino)diazen-1-ium-1,2-diolate,
O²-[1-(2,2-dimethylpropanoyl)piperidin-4-yl]1-(N-tert-butylamino)diazen-1-ium-1,2-diolate,
O²-{1-[(4-cyanophenyl)carbonyl]piperidin-4-yl}1-(N-tert-butylamino)diazen-1-ium-1,2-diolate,
O²-{1-[(2-methylphenyl)carbonyl]piperidin-4-yl}1-(N-tert-butylamino)diazen-1-ium-1,2-diolate,
(±)—O²-[1-(pyridin-4-ylcarbonyl)azepan-4-yl]1-(N-tert-butylamino)diazen-1-ium-1,2-diolate,
O²-[(3R)-1-(methylsulfonyl)pyrrolidin-3-yl]1-(N-tert-butylamino)diazen-1-ium-1,2-diolate,
O²-[1-(methylsulfonyl)piperidin-4-yl]1-(N-tert-butylamino)diazen-1-ium-1,2-diolate,
O²-[1-(tert-butylsulfonyl)piperidin-4-yl]1-(N-tert-butylamino)diazen-1-ium-1,2-diolate,
O²-[1-(5-cyanopyridin-2-yl)piperidin-4-yl]1-(N-tert-butylamino)diazen-1-ium-1,2-diolate,
O²-[1-(4-cyanopyridin-2-yl)piperidin-4-yl]1-(N-tert-butylamino)diazen-1-ium-1,2-diolate,
O²-[1-(3-cyanophenyl)piperidin-4-yl]1-(N-tert-butylamino)diazen-1-ium-1,2-diolate,
O²-[(3R)-1-(5-cyanopyrazin-2-yl)pyrrolidin-3-yl]1-(N-tert-butylamino)diazen-1-ium-1,2-diolate,
O²-[(3R)-1-(3-cyanophenyl)pyrrolidin-3-yl]1-(N-tert-butylamino)diazen-1-ium-1,2-diolate,
O²-{(3R)-1-[2-(trifluoromethyl)pyridin-3-yl]pyrrolidin-3-yl}1-(N-tert-butylamino)diazen-1-ium-1,2-diolate,
O²-[(3R)-1-(6-cyanopyridin-2-yl)pyrrolidin-3-yl]1-(N-tert-butylamino)diazen-1-ium-1,2-diolate,
O²-{(3R)-1-[3-(trifluoromethyl)phenyl]pyrrolidin-3-yl}1-(N-tert-butylamino)diazen-1-ium-1,2-diolate,
O²-[1-(5-chloropyridin-2-yl)piperidin-4-yl]1-(N-tert-butylamino)diazen-1-ium-1,2-diolate,
O²-[1-(5-carbamoylpyridin-2-yl)piperidin-4-yl]1-(N-tert-butylamino)diazen-1-ium-1,2-diolate,
O²-{(3R)-1-[3-(1H-1,2,3-triazol-1-yl)phenyl]pyrrolidin-3-yl}1-(N-tert-butylamino)diazen-1-ium-1,2-diolate,
O²-{1-[3-(1H-1,2,4-triazol-1-yl)phenyl]piperidin-4-yl}1-(N-tert-butylamino)diazen-1-ium-1,2-diolate,
O²-{1-[3-(1H-1,2,3-triazol-1-yl)phenyl]piperidin-4-yl}1-(N-tert-butylamino)diazen-1-ium-1,2-diolate,
O²-{1-[5-(1H-1,2,3-triazol-1-yl)pyridin-2-yl]piperidin-4-yl}1-(N-tert-butylamino)diazen-1-ium-1,2-diolate,
O²-(tetrahydro-2H-pyran-4-yl)1-(N-tert-butylamino)diazen-1-ium-1,2-diolate,
O²-[(3R)-1-(3-methylphenyl)-2-oxopyrrolidin-3-yl]1-(N-tert-butylamino)diazen-1-ium-1,2-diolate,
O²-{(3R)-2-oxo-1-[3-(trifluoromethoxy)phenyl]pyrrolidin-3-yl}1-(N-tert-butylamino)diazen-1-ium-1,2-diolate,
O²-[(3R)-1-(5-chloropyridin-3-yl)-2-oxopyrrolidin-3-yl]1-(N-tert-butylamino)diazen-1-ium-1,2-diolate,
O²-[(3R)-1-(5-cyanopyridin-2-yl)-2-oxopyrrolidin-3-yl]1-(N-tert-butylamino)diazen-1-ium-1,2-diolate, or
O²-{(3R)-2-oxo-1-[4-(trifluoromethyl)phenyl]pyrrolidin-3-yl}1-(N-tert-butylamino)diazen-1-ium-1,2-diolate,
or a pharmaceutically acceptable salt thereof.

In another embodiment, compounds of the invention are
O²-[1-(5-cyanopyridin-2-yl)piperidin-4-yl]1-(N-tert-butylamino)diazen-1-ium-1,2-diolate,
O²-[1-(4-cyanopyridin-2-yl)piperidin-4-yl]1-(N-tert-butylamino)diazen-1-ium-1,2-diolate,
O²-{(3R)-1-[2-(trifluoromethyl)pyridin-3-yl]pyrrolidin-3-yl}1-(N-tert-butylamino)diazen-1-ium-1,2-diolate,
O²-[(3R)-1-(6-cyanopyridin-2-yl)pyrrolidin-3-yl]1-(N-tert-butylamino)diazen-1-ium-1,2-diolate,
O²-[1-(5-chloropyridin-2-yl)piperidin-4-yl]1-(N-tert-butylamino)diazen-1-ium-1,2-diolate,
O²-[1-(5-carbamoylpyridin-2-yl)piperidin-4-yl]1-(N-tert-butylamino)diazen-1-ium-1,2-diolate,
O²-[(3R)-1-(5-chloropyridin-3-yl)-2-oxopyrrolidin-3-yl]1-(N-tert-butylamino)diazen-1-ium-1,2-diolate,
O²-[(3R)-1-(5-cyanopyridin-2-yl)-2-oxopyrrolidin-3-yl]1-(N-tert-butylamino)diazen-1-ium-1,2-diolate,
O²-{(3R)-2-oxo-1-[4-(trifluoromethyl)phenyl]pyrrolidin-3-yl}1-(N-tert-butylamino)diazen-1-ium-1,2-diolate,
or a pharmaceutically acceptable salt thereof.

Compounds of the invention can be used to treat hypertension, treat angina, improve insulin sensitivity, and provide renal protection. The compounds can be used alone or in combination (e.g., separate but co-administered, or administered in a fixed dose) with other antihypertensives such as, for example, angiotensin II receptor blockers, diuretics, ACE inhibitors, (3-blockers, and calcium channel blockers.

Pharmaceutically acceptable salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, carbonate, cyclopentanepropionate, digluconate, dodecylsulfate, ethanesulfonate, fumarate, glucoheptanoate, gluconate, glycerophosphate, hemisulfate, heptanoate, hexanoate, hippurate, hydrochloride, hydrobromide, hydroiodide, 2-hydroxyethanesulfonate, lactate, lactobionate, laurylsulfate, malate, maleate, mesylate, methanesulfonate, 2-naphthalenesulfonate, nicotinate, nitrate, oleate, oxalate, pamoate, pectinate, persulfate, 3-phenylpropionate, picrate, pivalate, propionate, stearate, succinate, sulfate, tartrate, thiocyanate, tosylate, and undecanoate. Additional specific anionic salts include ascorbate, gluceptate, glutamate, glucoronate, besylate, caprylate, isetionate, gentisate, malonate, napasylate, edfisylate, pamoate, xinafoate, and napadisylate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Additional specific cationic salts include tromethamine, benzathine, benethamine, diethylammonium, epolamine, hydrabamine.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof, are represented.

Some of the compounds described herein may exist as tautomers. The individual tautomers as well as mixtures thereof are encompassed with the described compounds.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g. "$\xi$—", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

The term "alkylene" refers to any divalent linear or branched chain aliphatic hydrocarbon radical having a number of carbon atoms in the specified range. Thus, for example, "—$C_1$-$C_6$ alkylene-" refers to any of the $C_1$ to $C_6$ linear or branched alkylenes, and "—$C_1$-$C_4$ alkylene-" refers to any of the $C_1$ to $C_4$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Another sub-class of interest is an alkylene selected from the group consisting of —$CH_2$—, —$CH(CH_3)$—, and —$C(CH_3)_2$—. Expressions such as "$C_1$-$C_4$ alkylene-phenyl" and "$C_1$-$C_4$ alkyl substituted with phenyl" have the same meaning and are used interchangeably.

Except where noted herein, alkyl groups and alkylene groups may be unsubstituted, or substituted with 1 to 3 substituents on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —OC(O)$C_1$-$C_6$ alkyl, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_0$-$C_6$ alkyl)C(O)NH—, $H_2$N—C(NH)—, —O($C_1$-$C_6$ alkyl)$CF_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

The term "aryl", alone or in combination, relates to a phenyl, naphthyl or indanyl group, preferably a phenyl group. The abbreviation "Ph" represents phenyl.

The term "carbocycle" (and variations thereof such as "carbocyclic" or "carbocyclyl") as used herein, unless otherwise indicated, refers to a $C_3$ to $C_8$ monocyclic saturated or unsaturated ring. The carbocycle may be attached to the rest of the molecule at any carbon atom which results in a stable compound. Saturated carbocyclic rings are also referred to as cycloalkyl rings, e.g., cyclopropyl, cyclobutyl, etc.

The term "heteroaryl" refers to an unsaturated ring having a specified number of atom members (e.g., 5 or 6-membered), including a specified number of heteroatoms (e.g., 1, 2, 3 or 4 heteroatoms independently selected from N, O or S), e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

The terms "heterocycle" and "heterocyclic" refer to a saturated monocyclic 5- to 8-membered ring having 1-4 heteroatoms selected from N, O and S, or a 7- to 12-membered saturated bicyclic ring system having 1-6 heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Except where noted herein, aryl groups and carbocycles may be unsubstituted, or substituted with 1, 2, or 3 substituents on any one or more available carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$($C_1$-$C_6$ alkyl)-, ($C_1$-$C_6$ alkyl)C(O)$_{1-2}$—, HC(O)$_{1-2}$($C_1$-$C_6$ alkyl)-, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, heteroaryl groups and heterocycles may be unsubstituted, or substituted with 1, 2, or 3 substituents on any one or more available carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2$N—C(NH)—, —O($C_1$-$C_6$ alkyl)$CF_3$, HC(O)—, ($C_1$-$C_6$ alkyl)C(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 or 2 substituents on any one or more available nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NH$C_1$-$C_6$ alkyl, —C(O)NH$_2$, —$C_1$-$C_6$ alkylC(O)NH$_2$, —$C_1$-$C_6$ alkyl OC(O)NH$_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound. Substituted heterocyclic rings include cyclic ureas, such as imidazolidin-2-one and tetrahydropyrimidin-2(1H)-one, which rings contain three sequential atoms that are nitrogen, carbon and nitrogen, wherein the carbon atom is substituted with an oxo substituent.

The compounds of the invention are useful for treating hypertension, Pulmonary Arterial Hypertension, congestive heart failure, angina, conditions resulting from excessive water retention, cardiovascular diseases, diabetes, oxidative stress, endothelial dysfunction, cirrhosis, pre-eclampsia, osteoporosis, or nephropathy, comprising administering a compounds of the invention to a patient having such a condition, or being at risk to having such condition The invention also relates to the use of compounds of the invention for the preparation of a medicament for the treatment and/or prophylaxis of the above-mentioned diseases.

The above-mentioned compounds of the invention are also of use in combination with other pharmacologically active compounds comprising angiotensin II receptor antagonists (e.g., losartan, valsartan, candesartan, irbesartan, olmesartan) angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S,5S,7S)—N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptor antagonists, vasodilators, calcium channel blockers (e.g., amlodipine, nifedipine, verapamril, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazosin, terazosin, prazosin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds including (i) PPAR-.gamma. agonists, such as the glitazones (e.g. troglitazone, pioglitazone, englitazone, MCC-555, rosiglitazone, balaglitazone, and the like) and other PPAR ligands, including PPAR.alpha./.gamma. dual agonists, such as KRP-297, muraglitazar, naveglitazar, Galida, tesaglitazar, TAK-559, PPAR.alpha. agonists, such as fenofibric acid derivatives (gemfibrozil, clofibrate, fenofibrate and bezafibrate), and selective PPAR.gamma. modulators (SPPAR.gamma.M's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors, glipizide, DPP-IV inhibitors such as sitagliptin, vildagliptin, alogliptin, and saxagliptin, which inhibit dipeptidyl peptidase-IV enzyme and which are useful for treating diabetes, or with other drugs beneficial for the prevention or the treatment of the above-mentioned diseases including nitroprusside and diazoxide. Such combination can be achieved by combining two active ingredients in a single dosage formulation containing two independent active ingredients, e.g., an angiotensin II receptor antagonist and a nitrooxy cyclopentane derivative of the invention.

The dosage regimen utilizing the compound of the invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds of the invention, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, more preferably 5 mg/day to 150 mg/day, and more preferably 5 mg/day to 100 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the compound of the invention may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The compounds of the invention can be administered in such oral forms as tablets, capsules and granules. The compounds of the invention are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose acetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

Methods of Synthesis

Several methods for preparing the compounds of this invention are described in the following Schemes and Examples. Starting materials and intermediates are made from known procedures or as otherwise illustrated. $R^{11}$ is nitrogen protecting group such as —$CH_2CH=CHR$ where R is, for example, hydrogen, $C_{1-6}$alkyl, e.g., —$C(CH_3)_3$, aryl, and $CH_2$aryl. M is an atom or groups that can be the counterion of the diazeniumdiolate salt, such as lithium, sodium, potassium, rubidium, cesium, magnesium, calcium, strontium, barium, or ammonium $R^{13}R^{14}R^{15}R^{16}N^+$ where $R^{13}$-$R^{16}$ is hydrogen or $C_{1-6}$alkyl. $R^{12}$ is, for example, methyl, $CF_3$ or substituted phenyl. X is Cl or —$OSO_2R^{12}$.

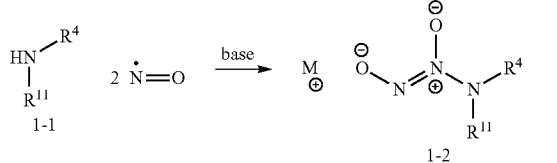

Scheme 1

Scheme 1 describes a convenient method to prepare the alkali metal diazeniumdiolates of the general structure 1-2 in this invention. The allyl amine 1-1 is treated with nitric oxide at an appropriate temperature such as room temperature in the presence of a suitable base such as sodium hydroxide, sodium methoxide, sodium tert-butoxide, sodium trimethylsilanolate, or the corresponding potassium bases, in an appropriate solvent such as acetonitrile, methanol, tetrahydrofuran, N,N-dimethylformamide, or water. Examples on the preparation of the sodium diazeniumdiolates can be found from the literature (Chakrapani, H.; Showalter, B. M.; Citro, M. L.; Keefer, L. K.; Saavedra, J. E. *Org. Lett.* 2007, 9, 4551-4554 and WO Patent 2009/094242.

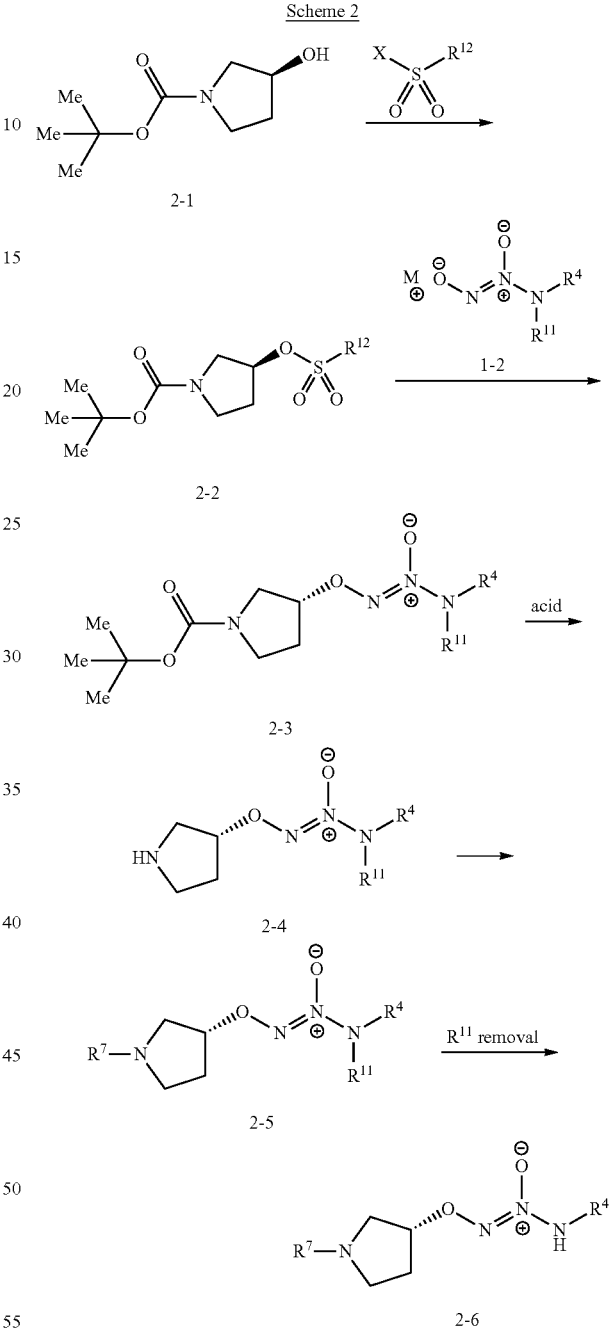

Scheme 2

Scheme 2 delineates a method to prepare $O^2$-alkylated diazeniumdiolates of the general structure 2-6 in this invention. tert-Butoxycarbonyl-protected pyrrolidinols of the general structure 2-1 can be activated for displacement at an appropriate temperature such as room temperature with a suitable reagent such as methanesulfonic anhydride, benzenesulfonyl chloride, 4-(trifluoromethyl)phenylsulfonyl chloride in the presence or absence of a base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone. The resultant sulfonate 2-2 can be displaced by an appropriate alkali metal diazeniumdiolate salt 1-2 at an appropriate temperature such as room temperature in an appropriate solvent such as dichloromethane, dichloroethane, chloroform, acetonitrile, tetrahydrofuran, dioxane, toluene, dimethoxyethane, N,N-dimethylformamide, or N-methylpyrrolidinone. The stereochemistry at the sulfonate carbon is typically inverted as a result of the displacement. The tert-butoxycarbonyl protective group can then be removed from product 2-3 with an acid such as hydrochloric acid, trifluoroacetic acid, or phosphoric acid to afford functionalized pyrrolidines 2-4. The desired group $R^7$ can be coupled to the pyrrolidine 2-4 using the appropriate method. For example, if $R^7$ is an aromatic or a heteroaromatic substituent, the appropriate aromatic or heteroaromatic halide can be coupled to 2-4 with the appropriate combination of palladium source, such as palladium(II)acetate, palladium (II) chloride, tris(dibenzylideneacetone) di(palladium), with the appropriate ligand such as triphenylphosphine, tri(tert-butyl)phosphine, tricyclohexylphosphine, racemic-2,2'-bis(diphenylphosphino)-1,1'-binaphthyl, 1,1'-bis(diphenylphosphino)ferrocene, 1,2-bis(diphenylphosphino)ethane, 1,2-bis(diphenylphosphino)propane, 2-(di-tert-butylphosphino)biphenyl, 2-dicyclohexylphosphino-2',6'-dimethoxy-1,1'-biphenyl, or an appropriate pallacycle, such as chloro[2-(dicyclohexylphosphino)-3,6-dimethoxy-2'-4'-6'-tri-1-propyl-1,1'-biphenyl][2-(2-aminoethyl)phenyl]palladium (II). Alternatively, if $R^7$ is an electron-deficient aromatic or heteroaromatic system, the coupling can be performed through nucleophilic aromatic by reacting the appropriate aromatic or heteroaromatic halide with 2-4 in the presence of an appropriate base, such as potassium carbonate, cesium carbonate, triethylamine at an elevated temperature. If $R^7$ is an acyl or a sulfonyl group, the corresponding acyl halide or sulfonyl halide can be used. If $R^7$ is a carbamoyl group, the corresponding isocyanate can be used. $R^{11}$ is removed as the last step. When $R^{11}$ is an allyl group, the product 2-5 can be deprotected with the appropriate combination of palladium or platinum source, such as palladium(II)acetate, palladium(II) chloride, tris(dibenzylideneacetone)di(palladium), dichloro (1,5-cyclooctadiene)platinum(II), with the appropriate ligand such as triphenylphosphine, tri(tert-butyl)phosphine, tricyclohexylphosphine, racemic-2,2'-bis(diphenylphosphino)-1,1'-binaphthyl, 1,1'-bis(diphenylphosphino)ferrocene, 1,2-bis(diphenylphosphino)ethane, 1,2-bis(diphenylphosphino)propane, 2-(di-tert-butylphosphino)biphenyl, 2-dicyclohexylphosphino-2',6'-dimethoxy-1,1'-biphenyl, or an appropriate pallacycle, such as chloro[2-(dicyclohexylphosphino)-3,6-dimethoxy-2'-4'-6'-tri-1-propyl-1,1'-biphenyl][2-(2-aminoethyl)phenyl]palladium(II), or a heterogeneous palladium or platinum source, such as palladium on carbon, poisoned palladium on calcium carbonate, platinum on carbon, sulfided platinum on carbon, in the presence of an appropriate scavenger, such as N,N'-dimethylbarbituric acid, dimedone, thiosalicyclic acid, or an appropriate hydrogen donor, such as hydrogen gas, formic acid, sodium borohydride, triethylsilane, tributylstannane.

Scheme 3

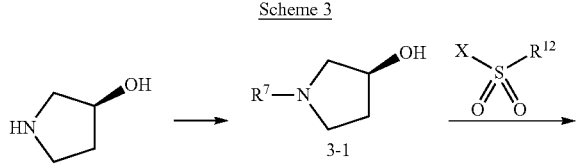

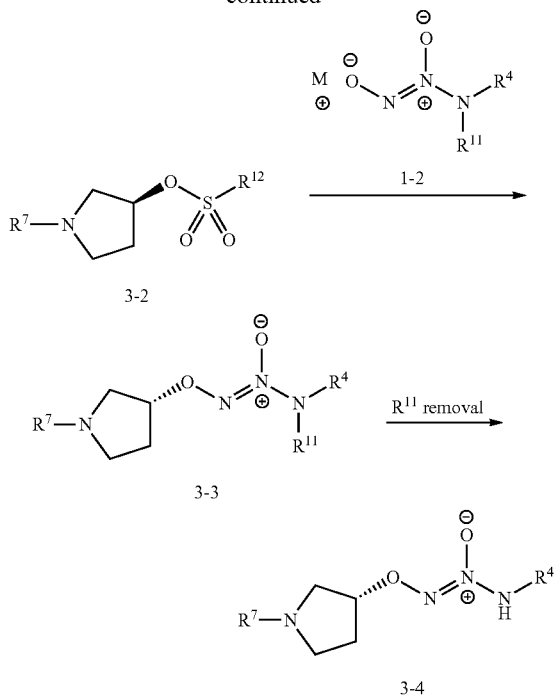

Scheme 3 describes an alternative method to prepare $O^2$-alkylated diazeniumdiolates of the general structure 3-4 in this invention. The steps are similar to those outlined in scheme 2, but the order of execution of those steps is modified. $R^7$ can be installed first on the pyrrolidinol, and the products 3-1 can be activated for displacement. The resultant sulfonates 3-2 can be displaced by an appropriate alkali metal diazeniumdiolate salt 1-2 to yield 3-3. $R^{11}$ is removed as the last step. Typical conditions for executing the transformations have been described above.

Example 1

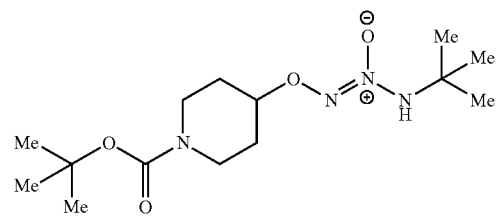 [SMILES: CC(C)(C)N/[N+]([O-])=N/OC1CCN(C(=O)OC(C)(C)C)CC1]

$O^2$-[1-(tert-butoxycarbonyl)piperidin-4-yl]1-(N-tert-butylamino)diazen-1-ium-1,2-diolate Step A: tert-butyl 4-({[4-(trifluoromethyl)phenyl]sulfonyl}oxy)piperidine-1-carboxylate To a stirring dichloromethane (50 mL) solution of tert-butyl 4-hydroxypiperidine-1-carboxylate (3.90 g, 19.4 mmol), 4-(dimethylamino)pyridine (0.23 g, 1.9 mmol), and triethylamine (8.0 mL, 57 mmol) was added 4-(trifluoromethyl)benzenesulfonyl chloride (4.75 g, 19.4 mmol). The reaction mixture was stirred for two hours at room temperature. The reaction was quenched with 1.0 M hydrochloric acid (100 mL) and extracted with diethyl ether (2×250 mL). The combined organic extracts were dried (magnesium sulfate), filtered and concentrated in vacuo to afford the crude product. It was used in the subsequent step without further purification. $^1$H NMR (500 MHz, CDCl$_3$) δ 8.06 (d, J=8.2 Hz, 2H), 7.83 (d, J=8.2 Hz, 2H), 4.79 (tt, J=7.6, 3.6 Hz, 1H), 3.62 (ddd, J=13.6, 7.4, 4.0 Hz, 2H), 3.27 (ddd, J=13.8, 7.8, 3.9 Hz, 2H), 1.86-1.79 (m, 2H), 1.75-1.68 (m, 2H), 1.44 (s, 9H).

Step B: O$^2$-[1-(tert-butoxycarbonyl)piperidin-4-yl]1-(N-tert-butyl-N-allylamino)diazen-1-ium-1,2-diolate To a stirring N,N-dimethylformamide (13 mL) solution of tert-butyl 4-({[4-(trifluoromethyl)phenyl]sulfonyl}oxy)piperidine-1-carboxylate (2.1 g, 5.1 mmol) at 50° C. was added sodium 1-(N-tert-butyl-N-allylamino)diazen-1-ium-1,2-diolate (1.0 g, 5.1 mmol). The reaction mixture was stirred at 50° C. for 2 hours. The reaction mixture was diluted with water (25 mL) and extracted with diethyl ether (4×40 mL). The combined organic extracts were dried (magnesium sulfate), filtered and concentrated in vacuo to afford the crude product. Chromatography over silica gel, eluting with hexanes/ethyl acetate, afforded the title compound as a colorless liquid. $^1$H NMR (500 MHz, CDCl$_3$) δ 5.77 (ddt, J=17.1, 10.0, 6.7 Hz, 1H), 5.27 (dd, J=17.1, 1.6 Hz, 1H), 5.15 (d, J=10.1 Hz, 1H), 4.48-4.41 (m, 1H), 3.83-3.73 (br s, 2H), 3.64 (d, J=6.8 Hz, 2H), 3.14 (ddd, J=13.6, 9.0, 3.6 Hz, 2H), 2.00-1.90 (br s, 2H), 1.75 (dtd, J=13.3, 8.7, 4.0 Hz, 2H), 1.45 (s, 9H), 1.26 (s, 9H); LC-MS: m/z 379.2 (M+Na).

Step C: O$^2$-[1-(tert-butoxycarbonyl)piperidin-4-yl]1-(N-tert-butylamino)diazen-1-ium-1,2-diolate To a stirring methanol (11.8 mL) solution of O$^2$-[1-(tert-butoxycarbonyl)piperidin-4-yl]1-(N-tert-butyl-N-allylamino)diazen-1-ium-1,2-diolate (422 mg, 1.19 mmol) was added sulfided platinum on carbon (5 weight %, 462 mg, 0.118 mmol). The reaction mixture was heated to 60° C. while stirring for 4 hours, and two batches of formic acid (91 μL, 2.1 mmol) were added every 2 hours. It was filtered through diatomaceous earth and concentrated in vacuo. Chromatography over silica gel, eluting with hexanes/ethyl acetate, afforded the title compound as a white solid. $^1$H NMR (500 MHz, CDCl$_3$) δ 5.82 (s, 1H), 4.39 (tt, J=8.6, 3.9 Hz, 1H), 4.05-3.65 (m, 2H), 3.16 (ddd, J=13.6, 9.2, 3.5 Hz, 2H), 2.12-1.86 (m, 2H), 1.79 (dtd, J=13.2, 8.9, 4.1 Hz, 2H), 1.48 (s, 9H), 1.33 (s, 9H); LC-MS: m/z 339.1 (M+Na).

Example 2

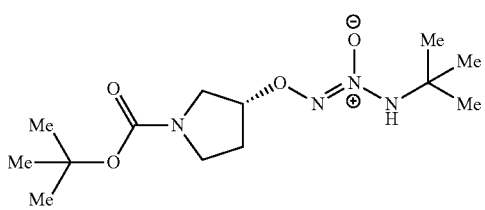 [SMILES: CC(C)(C)N/[N+]([O-])=N/O[C@@H]1CCN(C(=O)OC(C)(C)C)C1]

O$^2$-[(3R)-1-(tert-butoxycarbonyl)pyrrolidin-3-yl]1-(N-tert-butylamino)diazen-1-ium-1,2-diolate The title compound was made by following the procedures described in EXAMPLE 1, substituting tert-butyl (3S)-3-hydroxypyrrolidine-1-carboxylate for tert-butyl 4-hydroxypiperidine-1-carboxylate in step A. $^1$H NMR (500 MHz, CDCl$_3$) δ 5.95-5.89 (m, 1H), 4.87 (br s, 1H), 3.75-3.45 (m, 4H), 2.29-2.22 (m, 1H), 2.15-2.03 (m, 1H), 1.46 (s, 9H), 1.32 (s, 9H); LC-MS: m/z 303.2 (M+H).

Example 3

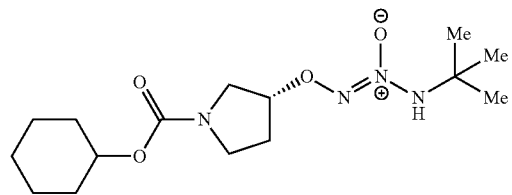 [SMILES: CC(C)(C)N/[N+]([O-])=N/O[C@@H]1CCN(C(=O)OC2CCCCC2)C1]

O$^2$-{(3R)-1-[(cyclohexyloxy)carbonyl]pyrrolidin-3-yl}1-(N-tert-butylamino)diazen-1-ium-1,2-diolate Step A: O$^2$-[(3R)-1-(tert-butoxycarbonyl)pyrrolidin-3-yl]1-(N-tert-butyl-N-allylamino)diazen-1-ium-1,2-diolate The title compound was made by following the procedures described in EXAMPLE 1, steps A and B, substituting tert-butyl (3S)-3-hydroxypyrrolidine-1-carboxylate for tert-butyl 4-hydroxypiperidine-1-carboxylate in step A. $^1$H NMR (500 MHz, CDCl$_3$) δ 5.81 (ddt, J=17.1, 10.0, 6.7 Hz, 1H), 5.30 (d, J=17.1 Hz, 1H), 5.20 (d, J=9.1 Hz, 1H), 4.95 (br s, 1H), 3.69-3.43 (m, 6H), 2.27 (dd, J=13.8, 6.4 Hz, 1H), 2.13-2.06 (m, 1H), 1.47 (s, 9H), 1.29 (s, 9H); LC-MS: m/z 365.1 (M+Na).

Step B: O$^2$-[(3R)-pyrrolidin-3-yl]1-(N-tert-butyl-N-allylamino)diazen-1-ium-1,2-diolate To a dichloromethane (8 mL) solution of O$^2$-[(3R)-1-(tert-butoxycarbonyl)pyrrolidin-3-yl]1-(N-tert-butyl-N-allylamino)diazen-1-ium-1,2-diolate (1.00 g, 2.92 mmol) at room temperature was added a 4.0 M dioxane solution of hydrochloric acid (1.46 mL, 5.84 mmol). The reaction mixture was stirred for 16 hours and concentrated in vacuo to afford the hydrochloride salt of the title compound. This crude product was used in the subsequent step without further purification. LC-MS: m/z 243.3 (M+H).

Step C: O$^2$-{(3R)-1-[(cyclohexyloxy)carbonyl]pyrrolidin-3-yl}1-(N-tert-butyl-N-allylamino) diazen-1-ium-1,2-diolate To a dichloromethane (4 mL) solution of O$^2$-[(3R)-pyrrolidin-3-yl]1-(N-tert-butyl-N-allylamino)diazen-1-ium-1,2-diolate (400 mg, 1.44 mmol) at room temperature was added triethylamine (0.60 mL, 4.3 mmol), followed by cyclohexyl chloroformate (350 mg, 2.15 mmol). After 2 hours, the reaction mixture was concentrated in vacuo. Chromatography over silica gel, eluting with hexanes/ethyl acetate, afforded the title compound as an oil. $^1$H NMR (500 MHz, CDCl$_3$) δ 5.78 (m, 1H), 5.28 (m, 1H), 5.16 (m, 1H), 4.94 (m, 1H), 4.66 (m, 1H), 3.71-3.20 (m, 6H), 2.23 (m, 1H), 2.05 (m, 1H), 1.80 (m, 2H), 1.70 (m, 2H), 1.50-1.20 (m, 15H); LC-MS: m/z 391.3 (M+Na).

Step D: O²-{(3R)-1-[(cyclohexyloxy)carbonyl]pyrrolidin-3-yl}1-(N-tert-butylamino)diazen-1-ium-1,2-diolate The title compound was made by following the procedures described in EXAMPLE 1, step C, substituting O²-{(3R)-1-[(cyclohexyloxy)carbonyl]pyrrolidin-3-yl}1-(N-tert-butyl-N-allylamino)diazen-1-ium-1,2-diolate for O²-[1-(tert-butoxycarbonyl)piperidin-4-yl]1-(N-tert-butyl-N-allylamino)diazen-1-ium-1,2-diolate. ¹H NMR (500 MHz, CDCl₃) δ 6.00 (bs, 1H), 4.85 (m, 1H), 4.64 (m, 1H), 3.73-3.45 (m, 4H), 2.23 (m, 1H), 2.09 (m, 1H), 1.80 (m, 2H), 1.70 (m, 2H), 1.50-1.20 (m, 15H); LC-MS: m/z 351.4 (M+Na).

Example 4

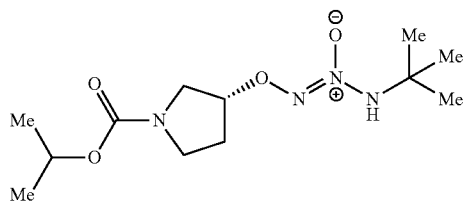 [SMILES: CC(C)OC(=O)N1CC[C@@H](O/N=[N+](\[O-])NC(C)(C)C)C1]

O²-{(3R)-1-[(propan-2-yloxy)carbonyl]pyrrolidin-3-yl}1-(N-tert-butylamino)diazen-1-ium-1,2-diolate The title compound was made by following the procedures described in EXAMPLE 3, substituting isopropyl chloroformate for cyclohexyl chloroformate in step C. ¹H NMR (500 MHz, CDCl₃) δ 6.14 (m, 1H), 4.80 (m, 2H), 3.62-3.35 (m, 4H), 2.14 (m, 1H), 2.00 (m, 1H), 1.19 (s, 9H), 1.12 (d, J=6.0 Hz, 6H); LC-MS: m/z 311.4 (M+Na).

Example 5

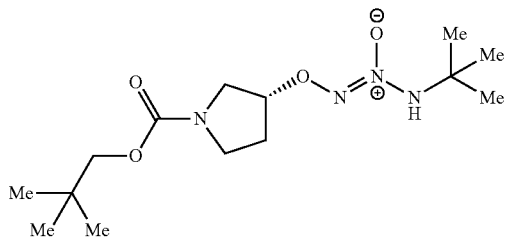 [SMILES: CC(C)(C)COC(=O)N1CC[C@@H](O/N=[N+](\[O-])NC(C)(C)C)C1]

O²-{(3R)-1-[(2,2-dimethylpropoxy)carbonyl]pyrrolidin-3-yl}1-(N-tert-butylamino)diazen-1-ium-1,2-diolate Step A: 2,2-dimethylpropyl (3S)-3-hydroxypyrrolidine-1-carboxylate To a mixture of dichloromethane (5 mL) and water (5 mL) was added sodium bicarbonate (0.96 g, 11 mmol), followed by (3S)-pyrrolidin-3-ol (1.00 g, 11.5 mmol). Neopentyl chloroformate (1.71 mL, 11.5 mmol) was then added dropwise, and the resulting suspension was stirred at room temperature for 1.5 hours. Chromatography over silica gel, eluting with hexanes/ethyl acetate, afforded the title compound. ¹H NMR (500 MHz, CDCl₃) δ 4.50 (br s, 1H), 3.81-3.77 (m, 2H), 3.59-3.41 (m, 4H), 2.07-1.96 (m, 2H), 1.75-1.72 (m, 1H), 0.97 (s, 9H).

Step B: O²-{(3R)-1-[(2,2-dimethylpropoxy)carbonyl]pyrrolidin-3-yl}1-(N-tert-butylamino) diazen-1-ium-1,2-diolate The title compound was made by following the procedures described in EXAMPLE 1, substituting 2,2-dimethylpropyl (3S)-3-hydroxypyrrolidine-1-carboxylate for tert-butyl 4-hydroxypiperidine-1-carboxylate in step A. ¹H NMR (500 MHz, CDCl₃) δ 6.00 (bs, 1H), 4.85 (m, 1H), 4.64 (m, 1H), 3.73-3.45 (m, 4H), 2.23 (m, 1H), 2.09 (m, 1H), 1.80 (m, 2H), 1.70 (m, 2H), 1.50-1.20 (m, 15H); LC-MS: m/z 339.4 (M+Na).

Example 6

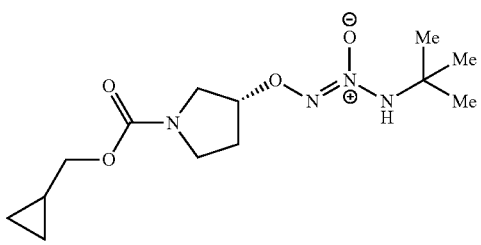 [SMILES: CC(C)(C)N/[N+]([O-])=N/O[C@@H]1CCN(C(=O)OCC2CC2)C1]

O²-{(3R)-1-[(cyclopropylmethoxy)carbonyl]pyrrolidin-3-yl}1-(N-tert-butylamino)diazen-1-ium-1,2-diolate Step A: O²-{(3R)-1-[(cyclopropylmethoxy)carbonyl]pyrrolidin-3-yl}1-(N-tert-butyl-N-allyl amino)diazen-1-ium-1,2-diolate To an acetonitrile (10 mL) solution of cyclopropanemethanol (0.71 mL, 9.0 mmol) and triethylamine (1.25 mL, 8.97 mmol) was added N,N-disuccinimidyl carbonate (1840 mg, 7.17 mmol). The resulting mixture was stirring at room temperature for 16 hours, then to it was added the hydrochloride salt of O²-[(3R)-pyrrolidin-3-yl]1-(N-tert-butyl-N-allylamino) diazen-1-ium-1,2-diolate (500 mg, 1.79 mmol), followed by another 2.5 equivalents of triethylamine. The reaction mixture was stirred at room temperature for another 4 hours. Chromatography over silica gel, eluting with hexanes/ethyl acetate, afforded the title compound. ¹H NMR (500 MHz, CDCl₃) δ 5.80 (m, 1H), 5.31 (m, 1H), 5.20 (m, 1H), 4.98 (m, 1H), 4.20 (d, J=7.4 Hz, 2H), 3.92 (m, 2H), 3.67 (m, 1H), 3.65 (m, 3H), 2.23 (m, 1H), 2.30 (m, 1H), 1.30 (s, 9H), 1.08 (m, 1H), 0.70 (m, 2H), 0.40 (m, 2H); LC-MS: m/z 363.4 (M+Na).

Step B: O²-{(3R)-1-[(cyclopropylmethoxy)carbonyl]pyrrolidin-3-yl}1-(N-tert-butylamino) diazen-1-ium-1,2-diolate The title compound was made by following the procedures described in EXAMPLE 1, step C, substituting O²-{(3R)-1-[(cyclopropylmethoxy)carbonyl]pyrrolidin-3-yl}1-(N-tert-butyl-N-allylamino)diazen-1-ium-1,2-diolate for O²-[1-(tert-butoxycarbonyl)piperidin-4-yl]1-(N-tert-butyl-N-allylamino)diazen-1-ium-1,2-diolate. ¹H NMR (500 MHz, CDCl$_3$) δ 6.00 (m, 1H), 4.84 (m, 1H), 3.85 (d, J=7.2 Hz, 2H), 3.70 (m, 1H), 3.60-3.46 (m, 3H), 2.24 (m, 1H), 2.07 (m, 1H), 1.26 (s, 9H), 1.08 (m, 1H), 0.49 (m, 2H), 0.22 (m, 2H); LC-MS: m/z 323.3 (M+Na).

Example 7

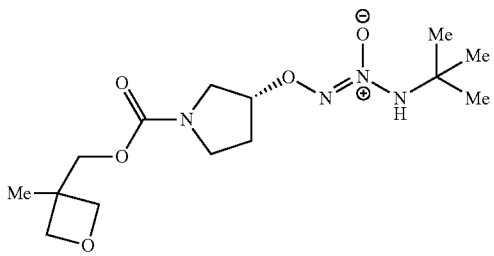 [SMILES: CC1(COC(=O)N2CC[C@@H](O/N=[N+](\[O-])NC(C)(C)C)C2)COC1]

O$^2$-[(3R)-1-{[(3-methyloxetan-3-yl)methoxy] carbonyl}pyrrolidin-3-yl]1-(N-tert-butylamino) diazen-1-ium-1,2-diolate The title compound was made by following the procedures described in EXAMPLE 6, substituting (3-methyloxetan-3-yl)methanol for cyclopropanemethanol in step A. $^1$H NMR (500 MHz, CDCl$_3$) δ 5.98 (m, 1H), 4.95 (m, 1H), 4.56 (m, 2H), 4.20 (m, 3H), 4.10 (m, 2H), 3.78 (m, 2H), 3.60 (m, 4H), 2.30 (m, 1H), 2.05 (m, 1H), 1.32 (s, 9H); LC-MS: m/z 331.4 (M+H).

Example 8

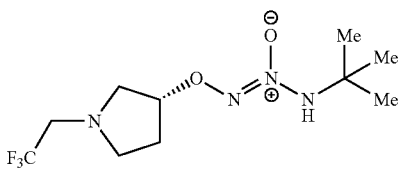 [SMILES: CC(C)(C)N/[N+]([O-])=N/O[C@@H]1CCN(CC(F)(F)F)C1]

O$^2$-[(3R)-1-(2,2,2-trifluoroethyl)pyrrolidin-3-yl]1-(N-tert-butylamino)diazen-1-ium-1,2-diolate Step A: O$^2$-[(3R)-1-(2,2,2-trifluoroethyl)pyrrolidin-3-yl]1-(N-tert-butyl-N-allylamino)diazen-1-ium-1,2-diolate To a N,N-dimethylformamide (10 mL) solution of the hydrochloride salt of O$^2$-[(3R)-pyrrolidin-3-yl]1-(N-tert-butyl-N-allylamino)diazen-1-ium-1,2-diolate (EXAMPLE 3, STEP B, 500 mg, 1.47 mmol) was added triethylamine (410 µL, 2.95 mmol) and 2,2,2-trifluoroethyl methanesulfonate (1.5 mmol). After 1 hour, the reaction mixture was diluted with dichloromethane (30 mL) and washed with brine. The organic layer was dried (sodium sulfate), filtered and concentrated in vacuo. Chromatography over silica gel, eluting with hexanes/ethyl acetate, afforded the title compound. $^1$H NMR (500 MHz, CDCl$_3$) δ 5.83 (m, 1H), 5.28 (d, 1H), 5.19 (d, 1H), 4.98 (m, 1H), 3.67 (d, J=6.7 Hz, 2H), 3.29 (m, 1H), 3.16 (q, J=9.5 Hz, 2H), 2.95 (m, 3H), 2.22-2.17 (m, 1H), 2.11-2.09 (m, 1H), 1.28 (s, 9H); LC-MS: m/z 325.1 (M+H).

Step B: O$^2$-[(3R)-1-(2,2,2-trifluoroethyl)pyrrolidin-3-yl]1-(N-tert-butylamino)diazen-1-ium-1,2-diolate The title compound was made by following the procedures described in EXAMPLE 1, step C, substituting O$^2$-[(3R)-1-(2,2,2-trifluoroethyl)pyrrolidin-3-yl]1-(N-tert-butyl-N-allylamino)diazen-1-ium-1,2-diolate for O$^2$-[1-(tert-butoxycarbonyl)piperidin-4-yl]1-(N-tert-butyl-N-allylamino)diazen-1-ium-1,2-diolate. $^1$H NMR (500 MHz, CDCl$_3$) δ 5.84 (s, 1H), 4.90-4.84 (m, 1H), 3.26 (dd, J=11.1, 6.2 Hz, 1H), 3.12 (q, J=9.5 Hz, 2H), 2.90-2.83 (m, 3H), 2.25-2.14 (m, 1H), 2.12-2.05 (m, 1H), 1.30 (s, 9H); LC-MS: m/z 285.2 (M+H).

Example 9

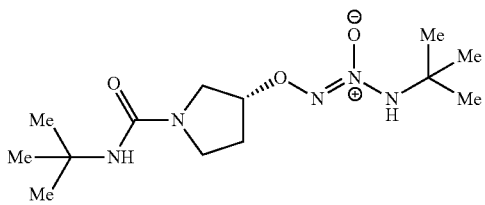 [SMILES: CC(C)(C)NC(=O)N1CC[C@@H](O/N=[N+](\[O-])NC(C)(C)C)C1]

O$^2$-[(3R)-1-(tert-butylcarbamoyl)pyrrolidin-3-yl]1-(N-tert-butylamino)diazen-1-ium-1,2-diolate Step A: (3S)-N-tert-butyl-3-hydroxypyrrolidine-1-carboxamide To a dichloromethane (200 mL) and diethyl ether (200 mL) solution of (S)-3-hydroxypyrrolidine (19.8 mL, 244 mmol) and triethylamine (45.0 mL, 323 mmol) at 0° C. was added tert-butyl isocyanate (28.0 mL, 245 mmol). The reaction mixture was stirred for 1 hour at 0° C., filtered, and concentrated in vacuo to afford the title compound as a white solid. This crude product was used in the subsequent step without further purification. $^1$H NMR (500 MHz, CDCl$_3$) δ 4.50-4.45 (m, 1H), 3.50-3.34 (m, 4H), 2.08-1.93 (m, 2H), 1.35 (s, 9H); LC-MS: m/z 187.3 (M+H).

Step B: O$^2$-[(3R)-1-(tert-butylcarbamoyl)pyrrolidin-3-yl]1-(N-tert-butylamino)diazen-1-ium-1,2-diolate The title compound was made by following the procedures described in EXAMPLE 1, substituting (3S)-N-tert-butyl-3-hydroxypyrrolidine-1-carboxamide for tert-butyl 4-hydroxypiperidine-1-carboxylate in step A. $^1$H NMR (500 MHz, CDCl$_3$) δ 5.87 (s, 1H), 4.90-4.85 (m, 1H), 4.02 (s, 1H), 3.66 (dt, J=12.1, 1.5 Hz, 1H), 3.58 (dd, J=12.1, 4.8 Hz, 1H), 3.47-3.38 (m, 2H), 2.33-2.26 (m, 1H), 2.16 (dtd, J=13.9, 9.4, 5.0 Hz, 1H), 1.34 (s, 9H), 1.31 (s, 9H); LC-MS: m/z 302.2 (M+H).

Example 10

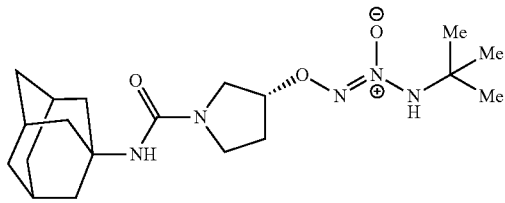 [SMILES: CC(C)(C)N/[N+]([O-])=N/O[C@@H]1CCN(C(=O)NC23CC4CC(CC(C4)C2)C3)C1]

O²-[(3R)-1-(tricyclo[3.3.1.1³,⁷]dec-1-ylcarbamoyl)pyrrolidin-3-yl]1-(N-tert-butylamino)diazen-1-ium-1,2-diolate The title compound was made by following the procedures described in EXAMPLE 9, substituting 1-adamantyl isocyanate for tert-butyl isocyanate in step A. ¹H NMR (500 MHz, CDCl₃) δ 5.89 (s, 1H), 4.90-4.92 (m, 1H), 3.93 (s, 1H), 3.68 (d, J=12.2 Hz, 1H), 3.62 (dd, J=12.2, 4.8 Hz, 1H), 3.49-3.42 (m, 2H), 2.42-2.31 (m, 1H), 2.22-2.15 (m, 1H), 2.10 (s, 3H), 2.01 (br s, 6H), 1.70 (m, 6H), 1.34 (s, 9H); LC-MS: m/z 402.1 (M+Na).

Example 11

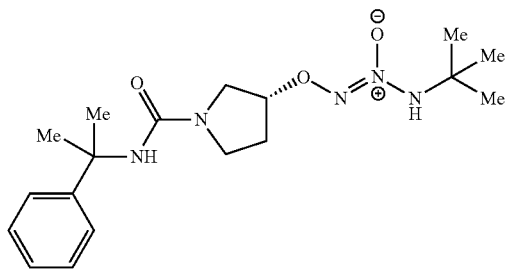 [SMILES: CC(C)(C)N/[N+]([O-])=N/O[C@@H]1CCN(C(=O)NC(C)(C)c2ccccc2)C1]

O²-{(3R)-1-[(2-phenylpropan-2-yl)carbamoyl]pyrrolidin-3-yl}1-(N-tert-butylamino)diazen-1-ium-1,2-diolate Step A: tert-butyl (3S)-3-[(phenylcarbonyl)oxy]pyrrolidine-1-carboxylate To a dichloromethane (100 mL) solution of benzoic acid (4.03 g, 33.0 mmol) and N-(3-dimethylaminopropyl)-N'-ethylcarbodiimide hydrochloride (10.4 g, 54.0 mmol) was added tert-butyl (3S)-3-hydroxypyrrolidine-1-carboxylate (5.62 g, 30.0 mmol). The reaction mixture was stirred for 6 hours at room temperature, diluted with water (200 mL) and charged with diethyl ether (200 mL). The combined organic extracts were washed with saturated aqueous sodium hydrogencarbonate, brine, dried (sodium sulfate) and concentrated in vacuo to afford the title compound. This crude product was used in the subsequent step without further purification.

Step B: (3S)-pyrrolidin-3-yl benzoate

To a dichloromethane (5 mL) solution of tert-butyl (3S)-3-[(phenylcarbonyl)oxy]pyrrolidine-1-carboxylate (2.62 g, 9.00 mmol) was added trifluoroacetic acid (5.55 mL, 72.0 mmol) dropwise. The reaction mixture was stirred at room temperature for 3 hours. Concentration of the reaction mixture in vacuo afforded the trifluoroacetate salt of the title compound. This crude product was used in the subsequent step without further purification.

Step C: (2-isocyanatopropane-2-yl)benzene

To a benzene (2 mL) solution of cumylamine (1.80 g, 13.3 mmol) and triethylamine (1.86 mL, 13.3 mmol) was added a 20% toluene solution of phosgene (17.5 mL, 33.3 mmol) dropwise. After completion, the reaction mixture was heated to 60° C. for 2 hours. It was then cooled to room temperature, charged with diethyl ether (20 mL), and filtered. Concentration of the filtrate in vacuo afforded the title compound. This crude product was used in the subsequent step without further purification.

Step D: (3S)-1-(2-phenylpropan-2-yl)pyrrolidin-3-yl benzoate

The title compound was made by following the procedures described in EXAMPLE 9, step A, substituting (3S)-pyrrolidin-3-yl benzoate for (S)-3-hydroxypyrrolidine and (2-isocyanatopropan-2-yl)benzene for tert-butyl isocyanate. ¹H NMR (500 MHz, CDCl₃) δ 8.03 (dd, J=8.4, 1.2 Hz, 2H), 7.59 (t, J=7.5 Hz, 1H), 7.46 (t, J=7.8 Hz, 2H), 7.42 (d, J=7.4 Hz, 2H), 7.32 (t, J=7.7 Hz, 2H), 7.22 (t, J=7.3 Hz, 1H), 5.57 (s, 1H), 4.61 (br s, 1H), 3.71 (dd, J=11.6, 4.8 Hz, 1H), 3.62-3.53 (m, 3H), 2.28-2.24 (m, 2H), 1.73 (s, 6H); LC-MS: m/z 353.0 (M+H).

Step E: (3S)-1-(2-phenylpropan-2-yl)pyrrolidin-3-ol

To a methanol (15 mL) solution of (3S)-1-(2-phenylpropan-2-yl)pyrrolidin-3-yl benzoate (2.50 g, 7.09 mmol) was added 4.0 M potassium hydroxide solution (3.19 mL, 12.8 mmol). The reaction mixture was stirred at room temperature for 2 hours and concentrated in vacuo. The residue was dissolved in dichloromethane (50 mL), washed with water (50 mL), dried (sodium sulfate), and concentrated in vacuo to afford the title compound as a white solid. This crude product was used in the subsequent step without further purification. ¹H NMR (500 MHz, CDCl₃) δ 7.42 (d, J=7.8 Hz, 2H), 7.32 (t, J=7.7 Hz, 2H), 7.21 (t, J=7.3 Hz, 1H), 4.52 (s, 1H), 4.40 (br s, 1H), 3.49-3.38 (m, 3H), 3.34 (d, J=11.0 Hz, 1H), 2.04-1.91 (m, 2H), 1.71 (s, 6H); LC-MS: m/z 249.2 (M+H).

Step F: O²-{(3R)-1-[(2-phenylpropan-2-yl)carbamoyl]pyrrolidin-3-yl}1-(N-tert-butylamino) diazen-1-ium-1,2-diolate The title compound was made by following the procedures described in EXAMPLE 1, substituting (3S)-1-(2-phenylpropan-2-yl)pyrrolidin-3-ol for tert-butyl 4-hydroxypiperidine-1-carboxylate in step A. ¹H NMR (500 MHz, CDCl₃) δ 7.45 (m, 2H), 7.35 (m, 2H), 7.24 (m, 1H), 5.90 (s, 1H), 4.92 (m, 1H), 4.52 (s, 1H), 3.71 (d, J=12.2 Hz, 1H), 3.65 (dd, J=12.2, 4.8 Hz, 1H), 3.55-3.49 (m, 2H), 2.38-2.33 (m, 1H), 2.25-2.17 (m, 1H), 1.73 (s, 3H), 1.74 (s, 3H), 1.34 (s, 9H); LC-MS: m/z 364 (M+H).

Example 12

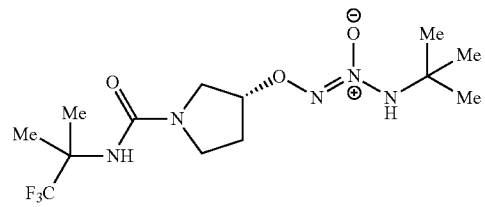 [SMILES: CC(C)(C)N/[N+]([O-])=N/O[C@@H]1CCN(C(=O)NC(C)(C)C(F)(F)F)C1]

O²-{(3R)-1-[(1,1,1-trifluoro-2-methylpropan-2-yl)carbamoyl]pyrrolidin-3-yl}1-(N-tert-butylamino)diazen-1-ium-1,2-diolate The title compound was made by following the procedures described in EXAMPLE 11, substituting 2,2,2-trifluoro-1,1- dimethylamine for cumylamine in step C. ¹H NMR (500 MHz, CDCl₃) δ 5.91 (s, 1H), 4.93 (t, J=4.6 Hz, 1H), 4.22 (s, 1H), 3.72 (d, J=12.2 Hz, 1H), 3.63 (dd, J=12.2 Hz, 4.6 Hz, 1H), 3.54-3.48 (m, 2H), 2.39-2.35 (m, 1H), 2.25-2.17 (m, 1H), 1.66 (s, 3H), 1.62 (s, 3H), 1.30 (s, 9H); LC-MS: m/z 356 (M+H).

Example 13

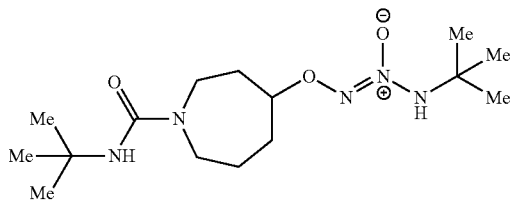 [SMILES: CC(C)(C)NC(=O)N1CCCC(O/N=[N+](\[O-])NC(C)(C)C)CC1]

(±)—O²-[1-(tert-butylcarbamoyl)azepan-4-yl]1-(N-tert-butylamino)diazen-1-ium-1,2-diolate Step A: (±)-tert-butyl 4-hydroxyazepane-1-carboxylate To a methanol (250 mL) solution of tert-butyl 4-oxoazepane-1-carboxylate (18.1 g, 85.0 mmol) at 0° C. was added sodium borohydride (8.01 g, 212 mmol). The reaction mixture was stirred for 2 hours before concentration in vacuo. The residue was dissolved in dichloromethane (250 mL) and washed with brine. The precipitate was removed by filtration, and the filtrate was dried (magnesium sulfate), filtered and concentrated in vacuo to afford the title compound. ¹H NMR (500 MHz, CDCl₃) 3.87 (br s, 1H), 3.49-3.18 (m, 4H), 2.05-1.48 (m, 6H), 1.46 (s, 9H); LC-MS: m/z 238.2 (M+Na).

Step B: (±)—O²-azepan-4-yl 1-(N-tert-butyl-N-allylamino)diazen-1-ium-1,2-diolate The title compound was made by following the procedures described in EXAMPLE 3, steps A and B, substituting (±)-tert-butyl 4-hydroxyazepane-1-carboxylate for tert-butyl (3S)-3-hydroxypyrrolidine-1-carboxylate in step A. ¹H NMR (500 MHz, CDCl₃) δ 9.86-9.50 (m, 2H), 5.75 (ddt, J=17.1, 10.0, 6.7 Hz, 1H), 5.26 (dd, J=17.0, 1.6 Hz, 1H), 5.14 (d, J=10.1 Hz, 1H), 4.67-4.61 (m, 1H), 3.63 (d, J=6.8 Hz, 2H), 3.42-3.15 (m, 4H), 2.42-2.27 (m, 2H), 2.18-2.01 (m, 3H), 1.91-1.82 (m, 1H), 1.25 (s, 9H); LC-MS: m/z 271.0 (M+H).

Step C: (±)—O²-[1-(tert-butylcarbamoyl)azepan-4-yl]1-(N-tert-butyl-N-allylamino)diazen-1-ium-1,2-diolate The title compound was made by following the procedures described in EXAMPLE 9, step A, substituting (±)—O²-azepan-4-yl 1-(N-tert-butyl-N-allylamino)diazen-1-ium-1,2-diolate for (S)-3-hydroxypyrrolidine. ¹H NMR (500 MHz, CDCl₃) δ 5.77 (ddt, J=17.1, 10.1, 6.7 Hz, 1H), 5.27 (dd, J=17.1, 1.6 Hz, 1H), 5.15 (d, J=10.1 Hz, 1H), 4.44 (tt, J=7.4, 3.8 Hz, 1H), 4.17 (br s, 1H), 3.64 (d, J=6.7 Hz, 2H), 3.49-3.39 (m, 3H), 3.27-3.19 (m, 1H), 2.15-2.07 (m, 1H), 2.03-1.88 (m, 4H), 1.72-1.58 (m, 1H), 1.35 (s, 9H), 1.26 (s, 9H); LC-MS: m/z 370.1 (M+H).

Step D: (±)—O²-[1-(tert-butylcarbamoyl)azepan-4-yl]1-(N-tert-butylamino)diazen-1-ium-1,2-diolate The title compound was made by following the procedures described in EXAMPLE 1, step C, substituting (±)—O²-[1-(tert-butylcarbamoyl)azepan-4-yl]1-(N-tert-butyl-N-allylamino)diazen-1-ium-1,2-diolate for 2-[1-(tert-butoxycarbonyl)piperidin-4-yl]1-(N-tert-butyl-N-allylamino)diazen-1-ium-1,2-diolate. ¹H NMR (500 MHz, CDCl₃) δ 5.81 (s, 1H), 4.39 (tt, J=7.6, 3.5 Hz, 1H), 4.21 (s, 1H), 3.55-3.47 (m, 1H), 3.45 (t, J=5.7 Hz, 2H), 3.30-3.23 (m, 1H), 2.19-2.11 (m, 1H), 2.07-1.93 (m, 4H), 1.76-1.60 (m, 1H), 1.38 (s, 9H), 1.33 (s, 9H); LC-MS: m/z 330.2 (M+H).

Example 14

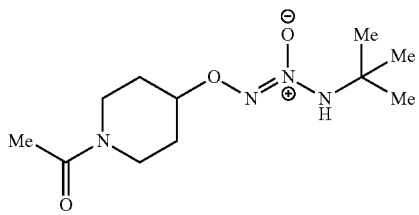 [SMILES: CC(=O)N1CCC(O/N=[N+](\[O-])NC(C)(C)C)CC1]

O²-(1-acetylpiperidin-4-yl)1-(N-tert-butylamino)diazen-1-ium-1,2-diolate

Step A: O²-(piperidin-4-yl)1-(N-tert-butyl-N-allylamino)diazen-1-ium-1,2-diolate The title compound was made by following the procedures described in EXAMPLE 3, steps A and B, substituting tert-butyl 4-hydroxypiperidine-1-carboxylate for tert-butyl (3S)-3-hydroxypyrrolidine-1-carboxylate in step A. ¹H NMR (500 MHz, CDCl₃) δ 5.76 (ddt, J=17.1, 10.1, 6.7 Hz, 1H), 5.26 (dd, J=17.0, 1.6 Hz, 1H), 5.13 (dd, J=10.1, 1.5 Hz, 1H), 4.65-4.55 (m, 1H), 3.63 (d, J=6.8 Hz, 2H), 3.36-3.16 (m, 4H), 2.36-2.26 (m, 2H), 2.23-2.17 (m, 2H), 1.25 (s, 9H); LC-MS: m/z 257.0 (M+H).

Step B: O²-(1-acetylpiperidin-4-yl)1-(N-tert-butyl-N-allylamino)diazen-1-ium-1,2-diolate To a dichloromethane (20 mL) solution of O²-(piperidin-4-yl)1-(N-tert-butyl-N-allylamino)diazen-1-ium-1,2-diolate (1.18 g, 4.03 mmol) and triethylamine (1.40 mL, 10.1 mmol) was added acetyl chloride (0.344 mL, 4.84 mmol). The reaction mixture was stirred at room temperature for 2 hours, diluted with diethyl ether (40 mL), filtered and concentrated in vacuo. Chromatography over silica gel, eluting with ethyl acetate/methanol, afforded the title compound. ¹H NMR (500 MHz, CDCl₃) δ 5.77 (ddt, J=17.1, 10.0, 6.7 Hz, 1H), 5.27 (dd, J=17.1, 1.6 Hz, 1H), 5.15 (dd, J=10.1, 1.5 Hz, 1H), 4.55-4.49 (m, 1H), 3.91 (ddd, J=13.5, 7.4, 4.1 Hz, 1H); 3.75-3.61 (m, 1H), 3.38 (ddd, J=13.7, 8.2, 3.9 Hz, 1H), 3.31 (ddd, J=13.9, 8.2, 3.7 Hz, 1H), 2.10 (s, 3H), 2.02-1.92 (m, 2H), 1.89-1.77 (m, 2H), 1.26 (s, 9H); LC-MS: m/z 299.0 (M+H).

Step C: O²-(1-acetylpiperidin-4-yl)1-(N-tert-butylamino)diazen-1-ium-1,2-diolate The title compound was made by following the procedures described in EXAMPLE 1, step C, substituting O²-(1-acetylpiperidin-4-yl)1-(N-tert-butyl-N-allyl amino)diazen-1-ium-1,2-diolate for 2-[1-(tert-butoxycarbonyl)piperidin-4-yl]1-(N-tert-butyl-N-allylamino)diazen-1-ium-1,2-diolate. ¹H NMR (500 MHz, CDCl₃) δ 5.87 (s, 1H), 4.45 (ddt, J=8.2, 7.6, 3.8 Hz, 1H), 3.98 (ddd, J=13.5, 7.1, 4.1 Hz, 1H), 3.73

(ddd, J=13.8, 7.1, 4.0 Hz, 1H), 3.42-3.30 (m, 2H), 2.12 (s, 3H), 2.05-1.95 (m, 2H), 1.95-1.74 (m, 2H), 1.32 (s, 9H); LC-MS: m/z 259.3 (M+H).

Example 15

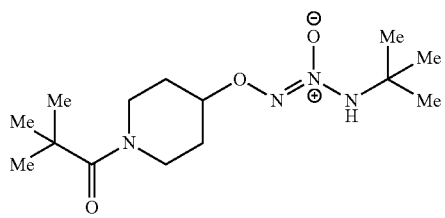 [SMILES: CC(C)(C)N/[N+]([O-])=N/OC1CCN(C(=O)C(C)(C)C)CC1]

$O^2$-[1-(2,2-dimethylpropanoyl)piperidin-4-yl]1-(N-tert-butylamino)diazen-1-ium-1,2-diolate The title compound was made by following the procedures described in EXAMPLE 14, substituting pivaloyl chloride for acetyl chloride in step B. $^1$H NMR (500 MHz, CDCl$_3$) δ 5.83 (s, 1H), 4.47 (tt, J=8.1, 3.9 Hz, 1H), 4.03 (ddd, J=13.5, 6.7, 3.8 Hz, 2H), 3.39 (ddd, J=13.7, 8.7, 3.4 Hz, 2H), 2.05-1.98 (m, 2H), 1.88-1.79 (m, 2H), 1.34 (s, 9H), 1.31 (s, 9H); LC-MS: m/z 301.1 (M+H).

Example 16

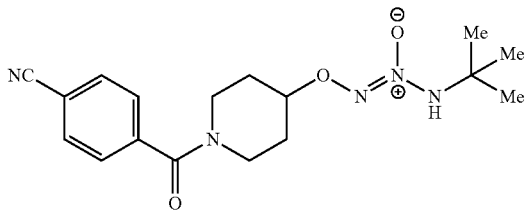 [SMILES: CC(C)(C)N/[N+]([O-])=N/OC1CCN(C(=O)c2ccc(C#N)cc2)CC1]

$O^2$-{1-[(4-cyanophenyl)carbonyl]piperidin-4-yl}1-(N-tert-butylamino)diazen-1-ium-1,2-diolate The title compound was made by following the procedures described in EXAMPLE 14, substituting 4-cyanobenzoyl chloride for acetyl chloride in step B. $^1$H NMR (500 MHz, CDCl$_3$) δ 7.75 (d, J=8.0 Hz, 2H), 7.52 (d, J=8.0 Hz, 2H), 5.87 (s, 1H), 4.56-4.50 (m, 1H), 4.20-3.94 (m, 1H), 3.65 (s, 2H), 3.44-3.13 (m, 1H), 2.16-2.01 (m, 1H), 2.10-1.85 (m, 2H), 1.98-1.72 (m, 1H), 1.34 (s, 9H); LC-MS: m/z 346.1 (M+H).

Example 17

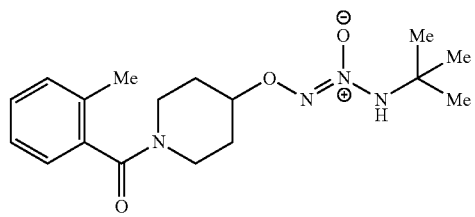 [SMILES: Cc1ccccc1C(=O)N1CCC(O/N=[N+](\[O-])NC(C)(C)C)CC1]

$O^2$-{1-[(2-methylphenyl)carbonyl]piperidin-4-yl}1-(N-tert-butylamino)diazen-1-ium-1,2-diolate The title compound was made by following the procedures described in EXAMPLE 14, substituting o-toluoyl chloride for acetyl chloride in step B. $^1$H NMR (500 MHz, CDCl$_3$) δ 7.31-7.27 (m, 1H), 7.24-7.17 (m, 2H), 7.15 (d, J=7.4 Hz, 1H), 5.82 (s, 1H), 4.47 (s, 1H), 4.24-4.00 (m, 1H), 3.68-3.42 (m, 2H), 3.13 (ddd, J=13.7, 8.2, 3.7 Hz, 1H), 2.30 (s, 3H), 2.15-2.05 (m, 1H), 2.00-1.85 (m, 2H), 1.80-1.70 (m, 1H), 1.31 (s, 9H); LC-MS: m/z 335.2 (M+H).

Example 18

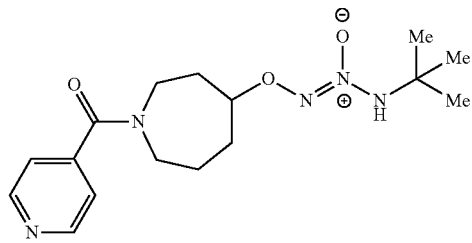 [SMILES: CC(C)(C)N/[N+]([O-])=N/OC1CCCN(C(=O)c2ccncc2)CC1]

(±)—$O^2$-[1-(pyridin-4-ylcarbonyl)azepan-4-yl]1-(N-tert-butylamino)diazen-1-ium-1,2-diolate The title compound was made by following the procedures described in EXAMPLE 14, substituting (±)—$O^2$-azepan-4-yl 1-(N-tert-butyl-N-allylamino)diazen-1-ium-1,2-diolate (EXAMPLE 13, step B) for $O^2$-(piperidin-4-yl)1-(N-tert-butyl-N-allylamino)diazen-1-ium-1,2-diolate and isonicotinoyl chloride hydrochloride for acetyl chloride in step B. $^1$H NMR (500 MHz, CDCl$_3$) δ 8.72-8.70 (m, 2H), 7.33-7.29 (m, 2H), 5.84 (s, 1H, R1), 5.82 (s, 1H, R2), 4.55-4.43 (m, 1H), 3.84-3.64 (m, 2H), 3.52-3.26 (m, 2H), 2.29-2.15 (m, 1H), 2.13-1.75 (m, 4H), 1.65-1.55 (m, 1H), 1.34 (s, 9H, R1), 1.32 (s, 9H, R2); LC-MS: m/z 336.1 (M+H).

Example 19

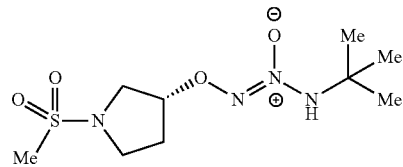 [SMILES: CC(C)(C)N/[N+]([O-])=N/O[C@@H]1CCN(S(C)(=O)=O)C1]

$O^2$-[(3R)-1-(methylsulfonyl)pyrrolidin-3-yl]1-(N-tert-butylamino)diazen-1-ium-1,2-diolate Step A: (3S)-1-(methylsulfonyl)pyrrolidin-3-yl methanesulfonate To a dichloromethane (200 mL) solution of (S)-3-hydroxypyrrolidine (5.0 g, 57 mmol) and triethylamine (24.0 mL, 172 mmol) at 0° C. was added methanesulfonyl chloride (7.23 g, 63.1 mmol). 4-(Dimethylamino)pyridine (0.70 g, 5.7 mmol) was then added, and the mixture was stirred at room temperature for 2 hours. It was diluted with dichloromethane (50 mL), and the combined organic layers were washed with aqueous 1

M hydrochloric acid (30 mL), water (30 mL), brine (30 mL), dried (magnesium sulfate), filtered and concentrated in vacuo to afford the title compound. The crude product was used in the subsequent step without further purification. $^1$H NMR (500 MHz, CDCl$_3$) δ 5.28 (t, J=4.5 Hz, 1H), 3.71 (d, J=12.9 Hz, 1H), 3.64 (dd, J=12.7, 4.0 Hz, 1H), 3.59 (td, J=9.2, 2.3 Hz, 1H), 3.46 (td, J=10.1, 6.7 Hz, 1H), 3.07 (s, 3H), 2.89 (s, 3H), 2.39-2.33 (m, 1H), 2.29-2.19 (m, 1H); LC-MS: m/z 244.1 (M+H).

Step B: O$^2$-[(3R)-1-(methylsulfonyl)pyrrolidin-3-yl] 1-(N-tert-butylamino)diazen-1-ium-1,2-diolate The title compound was made by following the procedures described in EXAMPLE 1, steps B and C, substituting (3S)-1-(methylsulfonyl)pyrrolidin-3-yl methanesulfonate for tert-butyl 4-({[4-(trifluoromethyl)phenyl]sulfonyl}oxy)piperidine-1-carboxylate in step B. $^1$H NMR (500 MHz, CDCl$_3$) δ 4.93 (br s, 1H), 3.74-3.55 (m, 3H), 3.46-3.39 (m, 1H), 2.87 (s, 3H), 2.40-2.33 (m, 1H), 2.24-2.15 (m, 1H), 1.33 (s, 9H); LC-MS: m/z 281.1 (M+H).

Example 20

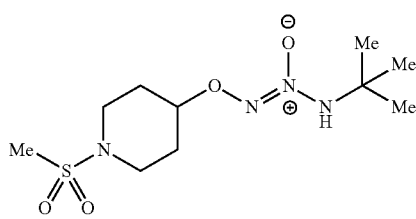 [SMILES: CC(C)(C)N/[N+]([O-])=N/OC1CCN(S(C)(=O)=O)CC1]

O$^2$-[1-(methylsulfonyl)piperidin-4-yl]1-(N-tert-butylamino)diazen-1-ium-1,2-diolate Step A: 1-(methylsulfonyl)piperidin-4-yl 4-(trifluoromethyl)benzenesulfonate To a dichloromethane (60 mL) solution of 4-hydroxypiperidine (2.00 g, 19.8 mmol) and triethylamine (4.13 mL, 29.7 mmol) at 0° C. was added methanesulfonic anhydride (3.10 g, 17.8 mmol). The reaction mixture was stirred for 1 hour, then to it was added 4-(dimethylamino)pyridine (0.242 g, 1.98 mmol), triethylamine (4.13 mL, 29.7 mmol), and 4-(trifluoromethyl)benzenesulfonyl chloride (5.32 g, 21.8 mmol). The reaction mixture was allowed to warm to room temperature, stirred for another hour, and concentrated in vacuo. Chromatography over silica gel, eluting with hexanes/ethyl acetate, afforded the title compound as a white solid. $^1$H NMR (500 MHz, CDCl$_3$) δ 8.06 (d, J=8.2 Hz, 2H), 7.85 (d, J=8.3 Hz, 2H), 4.84-4.79 (m, 1H), 3.36 (dt, J=12.3, 5.1 Hz, 2H), 3.27 (ddd, J=12.4, 8.3, 4.0 Hz, 2H), 2.79 (s, 3H), 2.11-1.90 (m, 4H); LC-MS: m/z 388.0 (M+H).

Step B: O$^2$-[1-(methylsulfonyl)piperidin-4-yl]1-(N-tert-butylamino)diazen-1-ium-1,2-diolate The title compound was made by following the procedures described in EXAMPLE 1, steps B and C, substituting 1-(methylsulfonyl)piperidin-4-yl 4-(trifluoromethyl)benzenesulfonate for tert-butyl 4-({[4-(trifluoromethyl)phenyl]sulfonyl}oxy)piperidine-1-carboxylate in step B. $^1$H NMR (500 MHz, CDCl$_3$) δ 5.89 (s, 1H), 4.49-4.43 (m, 1H), 3.42-3.30 (m, 4H), 2.81 (s, 3H), 2.09-2.04 (m, 4H), 1.34 (s, 9H); LC-MS: m/z 317.0 (M+Na).

Example 21

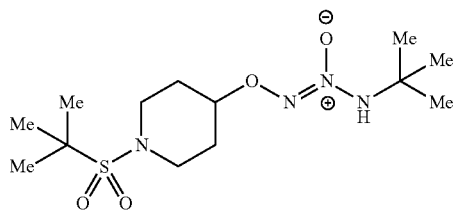 [SMILES: CC(C)(C)N/[N+]([O-])=N/OC1CCN(S(=O)(=O)C(C)(C)C)CC1]

O$^2$-[1-(tert-butylsulfonyl)piperidin-4-yl]1-(N-tert-butylamino)diazen-1-ium-1,2-diolate Step A: piperidin-4-yl 4-(trifluoromethyl)benzenesulfonate To a dichloromethane (10 mL) solution of tert-butyl 4-({[4-(trifluoromethyl)phenyl]sulfonyl}oxy)piperidine-1-carboxylate (EXAMPLE 1, STEP A, 1.20 g, 2.93 mmol) was added trifluoroacetic acid (500 μL, 6.73 mmol). The reaction mixture was stirred for 16 hours and concentrated in vacuo to afford the trifluoroacetate salt of the title compound. This crude product was used in the subsequent step without further purification. LC-MS: m/z 309.9 (M+H).

Step B: 1-(tert-butylsulfonyl)piperidin-4-yl 4-(trifluoromethyl)benzenesulfonate To a tetrahydrofuran (20 mL) solution of the trifluoroacetate salt of piperidin-4-yl 4-(trifluoromethyl)benzenesulfonate (800 mg, 1.97 mmol) at −78° C. was added tert-butylsulfinyl chloride (209 μL, 2.20 mmol). The reaction mixture was stirred for 10 minutes at −78° C. before triethylamine (1.10 mL, 7.88 mmol) was added. It was then stirred for another 2 hours at −78° C. Diethyl ether (50 mL) was added to the reaction mixture, and the combined organic layers were washed with 1 M hydrochloric acid (30 mL), water (30 mL), brine (30 mL), dried (sodium sulfate), filtered and concentrated in vacuo. The resulting oil was dissolved in dichloromethane (20 mL), cooled to 0° C., and m-chloroperbenzoic acid (374 mg, 2.17 mmol) was added to the solution. The ice-bath was removed, and the mixture was stirred at room temperature for 45 minutes. The reaction mixture was washed with saturated sodium bicarbonate (40 mL), water (40 mL), brine (40 mL), dried (magnesium sulfate), filtered and concentrated in vacuo. Chromatography over silica gel, eluting with hexanes/ethyl acetate, afforded the title compound.

Step C: O$^2$-[1-(tert-butylsulfonyl)piperidin-4-yl]1-(N-tert-butylamino)diazen-1-ium-1,2-diolate The title compound was made by following the procedures described in EXAMPLE 1, steps B and C, substituting 1-(tert-butylsulfonyl)piperidin-4-yl 4-(trifluoro methyl)benzenesulfonate for tert-butyl 4-({[4-(trifluoromethyl)phenyl]sulfonyl}oxy)piperidine-1-carboxylate in step B. $^1$H NMR (500 MHz, CDCl$_3$) δ 4.46 (br s, 1H), 3.64 (br s, 2H), 3.37 (br s, 2H), 2.13-2.01 (m, 2H), 2.03-1.82 (m, 2H), 1.38 (s, 9H), 1.33 (s, 9H); LC-MS: m/z 359.3 (M+Na).

Example 22

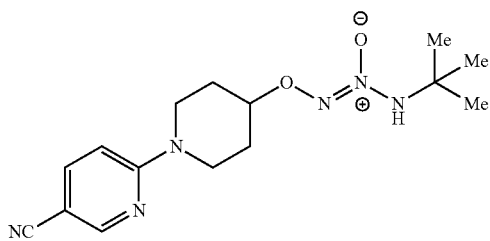 [SMILES: CC(C)(C)N/[N+]([O-])=N/OC1CCN(c2ccc(C#N)cn2)CC1]

O²-[1-(5-cyanopyridin-2-yl)piperidin-4-yl]1-(N-tert-butylamino)diazen-1-ium-1,2-diolate Step A:
6-(4-hydroxypiperidin-1-yl)pyridine-3-carbonitrile To a N,N-dimethylformamide (100 mL) solution of 2-chloro-5-cyanopyridine (36.2 g, 262 mmol) and 4-hydroxypiperidine (27.9 g, 275 mmol) was added potassium carbonate (40.1 g, 290 mmol). The reaction mixture was heated to 100° C. and stirred for 3 hours. It was cooled to room temperature, diluted with water (400 mL), and extracted with dichloromethane (3×250 mL). The combined organic extracts were washed with brine, dried (magnesium sulfate), and concentrated in vacuo to afford the title compound as a solid. This crude product was used in the subsequent step without further purification. ¹H NMR (500 MHz, CDCl₃) δ 8.39 (d, J=2.3 Hz, 1H), 7.58 (dd, J=9.1, 2.4 Hz, 1H), 6.62 (d, J=9.1 Hz, 1H), 4.10 (dt, J=13.6, 5.0 Hz, 2H), 4.01 (tt, J=8.3, 3.9 Hz, 1H), 3.37 (ddd, J=13.6, 9.2, 3.4 Hz, 2H), 2.61 (s, 1H), 1.99-1.92 (m, 2H), 1.62-1.53 (m, 2H); LC-MS: m/z 204.2 (M+H).

Step B: O²-[1-(5-cyanopyridin-2-yl)piperidin-4-yl]1-(N-tert-butylamino)diazen-1-ium-1,2-diolate The title compound was made by following the procedures described in EXAMPLE 1, substituting 6-(4-hydroxypiperidin-1-yl)pyridine-3-carbonitrile for tert-butyl 4-hydroxypiperidine-1-carboxylate in step A. ¹H NMR (500 MHz, CDCl₃) δ 8.42 (d, J=2.3 Hz, 1H), 7.64 (dd, J=9.1, 2.3 Hz, 1H), 6.67 (d, J=9.1 Hz, 1H), 5.84 (br s, 1H), 4.52 (tt, J=7.6, 3.9 Hz, 1H), 4.04 (ddd, J=13.6, 7.4, 3.9 Hz, 2H), 3.59 (ddd, J=13.7, 8.0, 3.7 Hz, 2H), 2.10-2.03 (m, 2H), 1.98-1.90 (m, 2H), 1.32 (s, 9H); LC-MS: m/z 319.1 (M+H).

Example 23

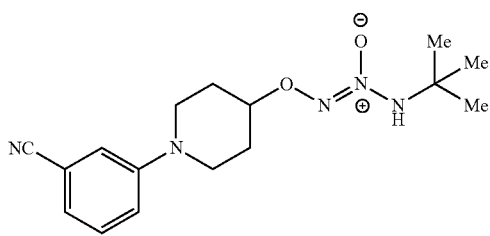 [SMILES: CC(C)(C)N/[N+]([O-])=N/OC1CCN(c2cccc(C#N)c2)CC1]

O²-[1-(3-cyanophenyl)piperidin-4-yl]1-(N-tert-butylamino)diazen-1-ium-1,2-diolate Step A: 3-(4-hydroxypiperidin-1-yl)benzonitrile To a toluene (140 mL) suspension of tris(dibenzylideneacetone)dipalladium (2.06 g, 2.25 mmol), 2-(di-tert-butylphosphino)biphenyl (0.839 g, 2.81 mmol), sodium tert-butoxide (4.05 g, 42.2 mmol) was added 3-bromobenzonitrile (5.11 g, 28.1 mmol), followed by 4-hydroxypiperidine (2.84 g, 28.1 mmol). The reaction mixture was heated to 80° C. for 5 hours while stirring under nitrogen. It was allowed to cool to room temperature, filtered, and concentrated in vacuo. Chromatography over silica gel, eluting with hexanes/ethyl acetate, afforded the title compound. ¹H NMR (500 MHz, CDCl₃) δ 7.33-7.24 (m, 1H), 7.15-7.10 (m, 2H), 7.06 (d, J=7.5 Hz, 1H), 3.95-3.87 (m, 1H), 3.57 (dt, J=12.7, 4.8 Hz, 2H), 3.00 (ddd, J=12.8, 9.5, 3.2 Hz, 2H), 2.05-1.95 (m, 2H), 1.73-1.59 (m, 2H); LC-MS: m/z 203.2 (M+H).

Step B: O²-[1-(5-cyanopyridin-2-yl)piperidin-4-yl]1-(N-tert-butylamino)diazen-1-ium-1,2-diolate The title compound was made by following the procedures described in EXAMPLE 1, substituting 3-(4-hydroxypiperidin-1-yl)benzonitrile for tert-butyl 4-hydroxypiperidine-1-carboxylate in step A. ¹H NMR (500 MHz, CDCl₃) δ 7.36-7.31 (m, 1H), 7.17-7.08 (m, 3H), 5.84 (s, 1H), 4.45 (tt, J=8.4, 3.9 Hz, 1H), 3.63-3.56 (m, 2H), 3.12 (ddd, J=12.9, 8.8, 3.4 Hz, 2H), 2.18-2.11 (m, 2H), 2.04-1.95 (m, 2H), 1.35 (s, 9H); LC-MS: m/z 318.2 (M+H).

Example 24

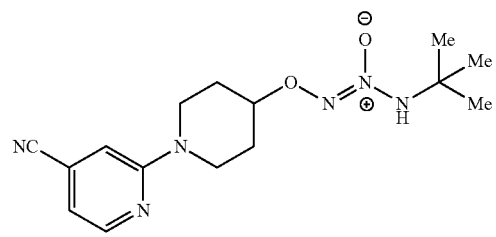 [SMILES: CC(C)(C)N/[N+]([O-])=N/OC1CCN(c2cc(C#N)ccn2)CC1]

O²-[1-(4-cyanopyridin-2-yl)piperidin-4-yl]1-(N-tert-butylamino)diazen-1-ium-1,2-diolate The title compound was made by following the procedures described in EXAMPLE 22, substituting 2-chloro-4-cyanopyridine for 2-chloro-5-cyanopyridine in step A. ¹H NMR (500 MHz, CDCl₃) δ 8.29 (d, J=5.0 Hz, 1H), 6.86 (s, 1H), 6.76 (d, J=5.0 Hz, 1H), 5.85 (s, 1H), 4.51 (tt, J=8.2, 3.9 Hz, 1H), 4.02 (ddd, J=13.4, 6.6, 4.0 Hz, 2H), 3.41 (ddd, J=13.5, 8.7, 3.6 Hz, 2H), 2.14-2.06 (m, 2H), 1.96-1.86 (m, 2H), 1.34 (s, 9H); LC-MS: m/z 319.3 (M+H).

Example 25

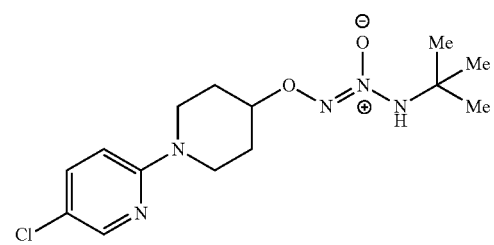 [SMILES: CC(C)(C)N/[N+]([O-])=N/OC1CCN(c2ccc(Cl)cn2)CC1]

O²-[1-(5-chloropyridin-2-yl)piperidin-4-yl]1-(N-tert-butylamino)diazen-1-ium-1,2-diolate The title compound was made by following the procedures described in EXAMPLE 22, substituting 2,5-dichloropyridine for 2-chloro-5-cyanopyridine in step A. ¹H NMR (500 MHz, CDCl₃) δ 8.10 (d, J=2.6 Hz, 1H), 7.42 (dd, J=9.0, 2.7 Hz, 1H), 6.62 (d, J=9.1 Hz, 1H), 5.80 (s, 1H), 4.45 (tt, J=8.5, 3.9 Hz, 1H), 4.00-3.93 (m, 2H), 3.32-3.25 (m, 2H), 2.11-2.04 (m, 2H), 1.92-1.83 (m, 2H), 1.31 (s, 9H); LC-MS: m/z 328.0 (M+H).

Example 26

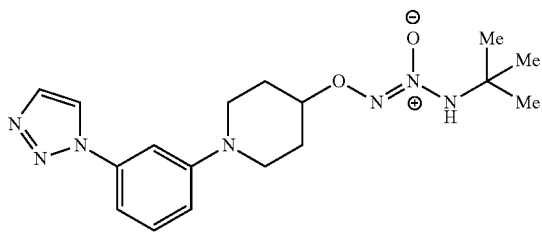 [SMILES: CC(C)(C)N/[N+]([O-])=N/OC1CCN(c2cccc(-n3ccnn3)c2)CC1]

O²-{1-[3-(1H-1,2,3-triazol-1-yl)phenyl]piperidin-4-yl}1-(N-tert-butylamino)diazen-1-ium-1,2-diolate Step A: 1-benzyl-4-{[tert-butyl(dimethyl)silyl]oxy}piperidine To a N,N-dimethylformamide (10 mL) solution of N-benzyl-4-hydroxypiperidine (1.90 g, 9.93 mmol) was added imidazole (1.35 g, 19.9 mmol) and tert-butyldimethylsilyl chloride (1.57 g, 10.4 mmol). After 1.5 hours, the reaction mixture was diluted with water and extracted with ethyl acetate (3×50 mL). The combined organic extracts were washed with brine (50 mL), dried (magnesium sulfate), filtered, and concentrated in vacuo. Chromatography over silica gel, eluting with hexanes/ethyl acetate, afforded the title compound. ¹H NMR (500 MHz, CDCl₃) δ 7.36-7.21 (m, 5H), 3.75-3.65 (m, 1H), 3.49 (s, 2H), 2.72-2.63 (m, 2H), 2.26-2.12 (m, 2H), 1.78-1.71 (m, 2H), 1.62-1.53 (m, 2H), 0.88 (s, 9H), 0.04 (s, 6H); LC-MS: m/z 306.1 (M+H).

Step B: 4-{[tert-butyl(dimethyl)silyl]oxy}piperidine

To a methanol (28 mL) solution of 1-benzyl-4-{[tert-butyl(dimethyl)silyl]oxy}piperidine (2.80 g, 9.18 mmol) was added palladium hydroxide on carbon (20 weight %, 280 mg. 0.40 mmol) and stirred under an atmospheric pressure of hydrogen for 16 hours. The reaction mixture was filtered through diatomaceous earth and washed with methanol. The filtrate was concentrated in vacuo to afford the title compound. This crude product was used in the subsequent step without further purification. ¹H NMR (500 MHz, CDCl₃) δ 3.77-3.70 (m, 1H), 3.09-3.02 (m, 2H), 2.61 (ddd, J=12.5, 9.5, 3.0 Hz, 2H), 1.82-1.72 (m, 2H), 1.42 (dtd, J=13.0, 9.0, 3.7 Hz, 2H), 0.89 (s, 9H), 0.05 (s, 6H); LC-MS: m/z 216.2 (M+H).

Step C: 4-{[tert-butyl(dimethyl)silyl]oxy}-1-[3-(1H-1,2,3-triazol-1-yl)phenyl]piperidine A dioxane (5 mL) solution of 1-(3-bromophenyl)-1H-1,2,3-triazole (224 mg, 1.00 mmol) and 4-{[tert-butyl(dimethyl)silyl]oxy}piperidine (323 mg, 1.50 mmol) was degassed with bubbling nitrogen in a vial. 2-(Dicyclohexylphosphino)-2'-(dimethylamino)biphenyl (20 mg, 0.051 mmol), palladium(II)acetate (11 mg, 0.050 mmol), and sodium tert-butoxide (384 mg, 4.0 mmol) were then added. The reaction mixture was degassed again, and the vial was sealed. It was heated to 100° C. for 20 hours and allowed to cool to room temperature. The reaction mixture was diluted with ethyl acetate, washed with water, brine, dried (magnesium sulfate), filtered, and concentrated in vacuo. Chromatography over silica gel, eluting with hexanes/ethyl acetate, afforded the title compound. ¹H NMR (500 MHz, CDCl₃) δ 7.96 (s, 1H), 7.83 (s, 1H), 7.38-7.31 (m, 2H), 7.02 (d, J=7.9 Hz, 1H), 6.98 (d, J=8.5 Hz, 1H), 3.97-3.89 (m, 1H), 3.53 (ddd, J=12.4, 7.5, 3.5 Hz, 2H), 3.16 (ddd, J=12.5, 7.8, 3.5 Hz, 2H), 1.95-1.81 (m, 2H), 1.72-1.64 (m, 2H), 0.90 (s, 9H), 0.08 (s, 6H); LC-MS: m/z 359.1 (M+H).

Step D: 1-[3-(1H-1,2,3-triazol-1-yl)phenyl]piperidin-4-ol

To an ethanol (18 mL) solution of 4-{[tert-butyl(dimethyl)silyl]oxy}-1-[3-(1H-1,2,3-triazol-1-yl)phenyl]piperidine (1.83 g, 5.12 mmol) was added concentrated hydrochloric acid (1030 µL, 12.5 mmol). After 6 hours, the reaction mixture was quenched with saturated aqueous sodium hydrogencarbonate solution (30 mL) and charged with ethyl acetate (30 mL). The reaction mixture was stirred vigorously for 10 minutes. The aqueous layer was extracted with more ethyl acetate (2×30 mL). The combined organic extracts were washed with brine, dried (magnesium sulfate), filtered, and concentrated in vacuo. Chromatography over silica gel, eluting with hexanes/ethyl acetate, afforded the title compound as a pale yellow oil. ¹H NMR (500 MHz, CDCl₃) δ 7.97 (s, 1H), 7.83 (s, 1H), 7.37 (s, 1H), 7.36 (t, J=8.1 Hz, 1H), 7.04 (d, J=8.0 Hz, 1H), 6.98 (d, J=8.5 Hz, 1H), 3.97-3.87 (m, 1H), 3.66 (dt, J=12.7, 4.7 Hz, 2H), 3.05 (ddd, J=12.7, 9.7, 3.1 Hz, 2H), 2.07-1.98 (m, 2H), 1.75-1.66 (m, 2H); LC-MS: m/z 245.2 (M+H).

Step E: O²-{1-[3-(1H-1,2,3-triazol-1-yl)phenyl]piperidin-4-yl}1-(N-tert-butylamino)diazen-1-ium-1,2-diolate The title compound was made by following the procedures described in EXAMPLE 1, substituting 1-[3-(1H-1,2,3-triazol-1-yl)phenyl]piperidin-4-ol for tert-butyl 4-hydroxypiperidine-1-carboxylate in step A. ¹H NMR (500 MHz, CDCl₃) δ 7.97 (s, 1H), 7.83 (s, 1H), 7.37 (s, 1H), 7.36 (t, J=8.1 Hz, 1H), 7.06 (d, J=7.7 Hz, 1H), 6.98 (dd, J=8.4, 2.4 Hz, 1H), 5.82 (s, 1H), 4.44 (tt, J=8.5, 3.9 Hz, 1H), 3.66 (dt, J=12.8, 5.0 Hz, 2H), 3.14 (ddd, J=12.8, 9.0, 3.3 Hz, 2H), 2.21-2.08 (m, 2H), 2.04-1.95 (m, 2H), 1.32 (s, 9H); LC-MS: m/z 360.2 (M+H).

Example 27

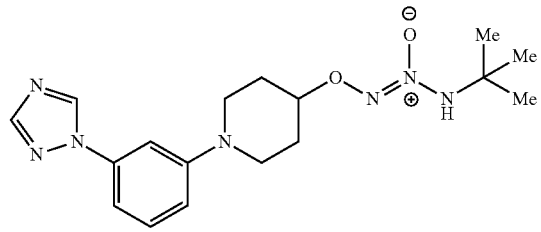 [SMILES: CC(C)(C)N/[N+]([O-])=N/OC1CCN(c2cccc(-n3cncn3)c2)CC1]

O²-{1-[3-(1H-1,2,4-triazol-1-yl)phenyl]piperidin-4-yl}1-(N-tert-butylamino)diazen-1-ium-1,2-diolate The title compound was made by following the procedures described in EXAMPLE 26, substituting 1-(3-bromophenyl)-

1H-1,2,4-triazole for 1-(3-bromophenyl)-1H-1,2,3-triazole in step C. ¹H NMR (500 MHz, CDCl₃) δ 8.53 (s, 1H), 8.09 (s, 1H), 7.35 (t, J=8.2 Hz, 1H), 7.31-7.24 (m, 1H), 7.05 (br s, 1H), 6.95 (br s, 1H), 5.82 (s, 1H), 4.47-4.40 (m, 1H), 3.65 (dt, J=12.6, 5.0 Hz, 2H), 3.17-3.08 (m, 2H), 2.20-2.09 (m, 2H), 2.04-1.96 (m, 2H), 1.32 (s, 9H); LC-MS: m/z 328.0 (M+H).

Example 28

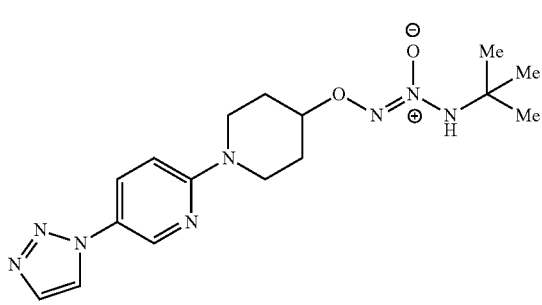 [SMILES: CC(C)(C)N/[N+]([O-])=N/OC1CCN(c2ccc(-n3ccnn3)cn2)CC1]

O²-{1-[5-(1H-1,2,3-triazol-1-yl)pyridin-2-yl]piperidin-4-yl}1-(N-tert-butylamino)diazen-1-ium-1,2-diolate The title compound was made by following the procedures described in EXAMPLE 22, substituting 2-fluoro-5-(1H-1,2,3-triazol-1-yl)pyridine for 2-chloro-5-cyano pyridine in step A. ¹H NMR (500 MHz, CDCl₃) δ 8.44 (d, J=2.7 Hz, 1H), 7.90-7.81 (m, 3H), 6.79 (d, J=9.1 Hz, 1H), 5.85 (s, 1H), 4.50 (tt, J=8.2, 3.8 Hz, 1H), 4.06 (ddd, J=13.5, 6.5, 3.9 Hz, 2H), 3.43 (ddd, J=13.5, 8.7, 3.4 Hz, 2H), 2.15-2.05 (m, 2H), 1.96-1.87 (m, 2H), 1.31 (s, 9H); LC-MS: m/z 361.1 (M+H).

Example 29

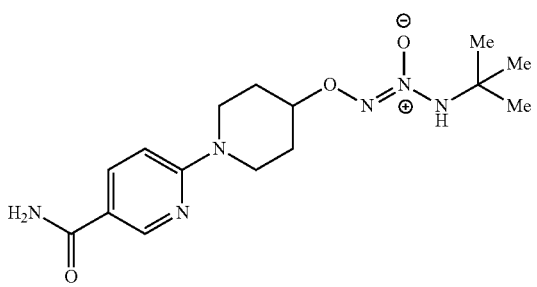 [SMILES: CC(C)(C)N/[N+]([O-])=N/OC1CCN(c2ccc(C(N)=O)cn2)CC1]

O²-[1-(5-carbamoylpyridin-2-yl)piperidin-4-yl]1-(N-tert-butylamino)diazen-1-ium-1,2-diolate To a water (2 mL)/methanol (2 mL) solution of O²-[1-(5-cyanopyridin-2-yl)piperidin-4-yl]1-(N-tert-butylamino)diazen-1-ium-1,2-diolate (EXAMPLE 22, 200 mg, 0.628 mmol) was added sodium perborate tetrahydrate (483 mg, 3.14 mmol). The reaction mixture was then heated to 50° C. for 18 hours, diluted with water (5 mL) and extracted with ethyl acetate (2×10 mL). The combined organic extracts were washed with brine, dried (magnesium sulfate), and concentrated in vacuo to afford the title compound. ¹H NMR (500 MHz, (CD₃)₂SO) δ 8.56 (d, J=2.3 Hz, 1H), 8.02 (dd, J=9.1, 2.4 Hz, 1H), 7.82 (s, 1H), 7.21 (s, 1H), 7.00 (d, J=9.1 Hz, 1H), 4.50-4.20 (m, 1H), 4.04 (dt, J=13.7, 4.8 Hz, 2H), 3.45-3.33 (m, 2H), 2.04-1.95 (m, 2H), 1.69-1.59 (m, 2H), 1.18 (s, 9H); LC-MS: m/z 337.0 (M+H).

Example 30

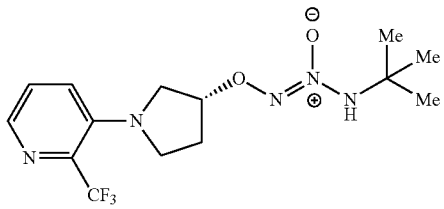 [SMILES: CC(C)(C)N/[N+]([O-])=N/O[C@@H]1CCN(c2cccnc2C(F)(F)F)C1]

O²-{(3R)-1-[2-(trifluoromethyl)pyridin-3-yl]pyrrolidin-3-yl}1-(N-tert-butylamino)diazen-1-ium-1,2-diolate Step A: O²-{(3R)-1-[2-(trifluoromethyl)pyridin-3-yl] pyrrolidin-3-yl}1-(N-tert-butyl-N-allyl amino)diazen-1-ium-1,2-diolate The title compound was made by following the procedures described in EXAMPLE 23, step A, substituting O²-[(3R)-pyrrolidin-3-yl]1-(N-tert-butyl-N-allylamino) diazen-1-ium-1,2-diolate (EXAMPLE 3, STEP B) for 4-hydroxypiperidine and 3-bromo-2-(trifluoromethyl)pyridine for 3-bromobenzonitrile. ¹H NMR (500 MHz, CDCl₃) δ 8.25-8.03 (m, 1H), 7.31-7.27 (m, 2H), 5.73 (ddt, J=17.1, 10.0, 6.7 Hz, 1H), 5.18 (d, J=17.0 Hz, 1H), 5.07-5.00 (m, 2H), 3.84 (dd, J=11.9, 4.8 Hz, 1H), 3.65-3.48 (m, 4H), 3.35 (td, J=8.5, 2.4 Hz, 1H), 2.40-2.34 (m, 1H), 2.29-2.19 (m, 1H), 1.22 (s, 9H); LC-MS: m/z 388.1 (M+H).

Step B: O²-{(3R)-1-[2-(trifluoromethyl)pyridin-3-yl] pyrrolidin-3-yl}1-(N-tert-butylamino) diazen-1-ium-1,2-diolate The title compound was made by following the procedures described in EXAMPLE 1, step C, substituting O²-{(3R)-1-[2-(trifluoromethyl)pyridin-3-yl]pyrrolidin-3-yl}1-(N-tert-butyl-N-allylamino)diazen-1-ium-1,2-diolate for O²-[1-(tert-butoxycarbonyl)piperidin-4-yl]1-(N-tert-butyl-N-allylamino)diazen-1-ium-1,2-diolate. ¹H NMR (500 MHz, CDCl₃) δ 8.19-8.14 (m, 1H), 7.35-7.31 (m, 2H), 5.06-4.92 (m, 1H), 3.88-3.81 (m, 1H), 3.65-3.53 (m, 2H), 3.41-3.34 (m, 1H), 2.49-2.28 (m, 1H), 2.30-2.21 (m, 1H), 1.29 (s, 9H); LC-MS: m/z 348.1 (M+H).

Example 31

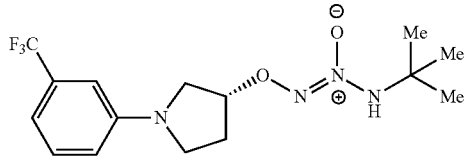 [SMILES: CC(C)(C)N/[N+]([O-])=N/O[C@@H]1CCN(c2cccc(C(F)(F)F)c2)C1]

O²-{(3R)-1-[3-(trifluoromethyl)phenyl]pyrrolidin-3-yl}1-(N-tert-butylamino)diazen-1-ium-1,2-diolate The title compound was made by following the procedures described in EXAMPLE 30, substituting 3-bromo-2-(trifluoromethyl)pyridine for 3-bromo-2-(trifluoromethyl)pyridine in step A. ¹H NMR (500 MHz, CDCl₃) δ 7.30 (t, J=8.0 Hz, 1H), 6.93 (d, J=7.7 Hz, 1H), 6.74 (s, 1H), 6.70 (d, J=8.5 Hz, 1H), 5.86 (s, 1H), 5.07-5.03 (m, 1H), 3.67 (dd, J=11.4, 5.0 Hz, 1H), 3.59 (d, J=11.4 Hz, 1H), 3.53 (td, J=9.1, 7.0 Hz, 1H), 3.45 (td, J=8.9, 2.9 Hz, 1H), 2.47-2.41 (m, 1H), 2.34-2.25 (m, 1H), 1.31 (s, 9H); LC-MS: m/z 347.1 (M+H).

Example 32

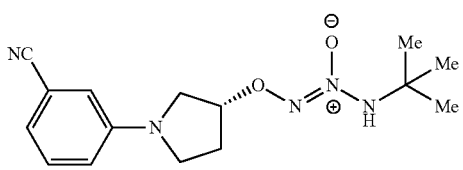 [SMILES: CC(C)(C)N/[N+]([O-])=N/O[C@@H]1CCN(c2cccc(C#N)c2)C1]

O²-[(3R)-1-(3-cyanophenyl)pyrrolidin-3-yl]1-(N-tert-butylamino)diazen-1-ium-1,2-diolate The title compound was made by following the procedures described in EXAMPLE 30, substituting 3-bromobenzonitrile for 3-bromo-2-(trifluoromethyl)pyridine in step A. ¹H NMR (500 MHz, CDCl₃) δ 7.31-7.26 (m, 1H), 6.96 (d, J=7.4 Hz, 1H), 6.80-6.67 (m, 2H), 5.93 (s, 1H), 5.12-5.00 (m, 1H), 3.64 (dd, J=11.3, 4.9 Hz, 1H), 3.57 (d, J=11.5 Hz, 1H), 3.51 (td, J=9.3, 6.9 Hz, 1H), 3.43 (td, J=8.8, 2.8 Hz, 1H), 2.49-2.42 (m, 1H), 2.35-2.26 (m, 1H), 1.32 (s, 9H); LC-MS: m/z 304.2 (M+H).

Example 33

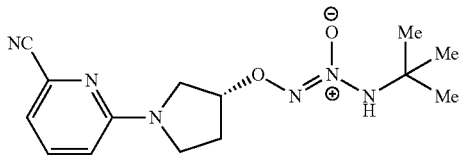 [SMILES: CC(C)(C)N/[N+]([O-])=N/O[C@@H]1CCN(c2cccc(C#N)n2)C1]

O²-[(3R)-1-(6-cyanopyridin-2-yl)pyrrolidin-3-yl]1-(N-tert-butylamino)diazen-1-ium-1,2-diolate The title compound was made by following the procedures described in EXAMPLE 22, substituting 6-fluoropyridine-2-carbonitrile for 2-chloro-5-cyanopyridine and (S)-3-hydroxypyrrolidine for 4-hydroxypiperidine in step A. ¹H NMR (500 MHz, CDCl₃) δ 7.47 (t, J=8.0 Hz, 1H), 6.93 (d, J=7.2 Hz, 1H), 6.53 (d, J=8.7 Hz, 1H), 5.90 (s, 1H), 5.04-4.99 (m, 1H), 3.93-3.84 (m, 2H), 3.70 (dd, J=12.8, 4.7 Hz, 1H), 3.62-3.55 (m, 1H), 2.48-2.39 (m, 1H), 2.31-2.21 (m, 1H), 1.30 (s, 9H); LC-MS: m/z 305.1 (M+H).

Example 34

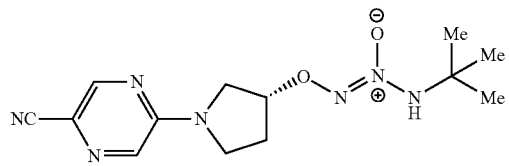 [SMILES: CC(C)(C)N/[N+]([O-])=N/O[C@@H]1CCN(c2cnc(C#N)cn2)C1]

O²-[(3R)-1-(5-cyanopyrazin-2-yl)pyrrolidin-3-yl]1-(N-tert-butylamino)diazen-1-ium-1,2-diolate The title compound was made by following the procedures described in EXAMPLE 22, substituting 5-bromopyrazine-2-carbonitrile for 2-chloro-5-cyanopyridine and O²-[(3R)-pyrrolidin-3-yl]1-(N-tert-butyl-N-allylamino)diazen-1-ium-1,2-diolate (EXAMPLE 3, STEP B) for 4-hydroxypiperidine in step A. ¹H NMR (500 MHz, CDCl₃) δ 8.36 (s, 1H), 7.91 (s, 1H), 5.19 (br s, 1H), 4.10-3.70 (m, 4H), 2.60-2.50 (m, 1H), 2.40-2.30 (m, 1H), 1.33 (s, 9H); LC-MS: m/z 306.3 (M+H).

Example 35

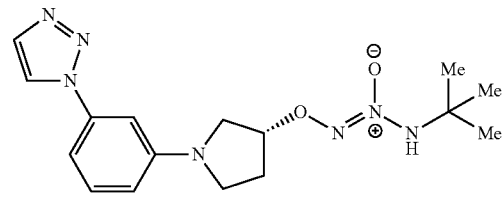 [SMILES: CC(C)(C)N/[N+]([O-])=N/O[C@@H]1CCN(c2cccc(-n3ccnn3)c2)C1]

O²-{(3R)-1-[3-(1H-1,2,3-triazol-1-yl)phenyl]pyrrolidin-3-yl}1-(N-tert-butylamino)diazen-1-ium-1,2-diolate The title compound was made by following the procedures described in EXAMPLE 30, substituting 1-(3-bromophenyl)-1H-1,2,3-triazole for 3-bromo-2-(trifluoromethyl)pyridine in step A. ¹H NMR (500 MHz, CDCl₃) δ 8.0-6.6 (m, 6H), 5.92 (s, 1H), 5.08 (br s, 1H), 3.8-3.5 (m, 4H), 2.6-2.1 (m, 2H), 1.33 (s, 9H); LC-MS: m/z 368.1 (M+Na).

Example 36

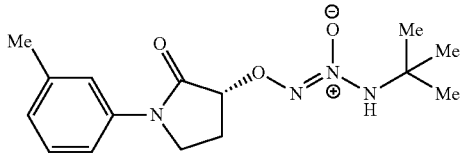 [SMILES: Cc1cccc(N2CC[C@@H](O/N=[N+](\[O-])NC(C)(C)C)C2=O)c1]

O²-[(3R)-1-(3-methylphenyl)-2-oxopyrrolidin-3-yl]1-(N-tert-butylamino)diazen-1-ium-1,2-diolate Step A: (3S)-3-hydroxy-1-(3-methylphenyl)pyrrolidin-2-one (S)-3-Hydroxypyrrolidin-2-one (1.52 g, 15.0 mmol), 3-bromotoluene (2.57 g, 15.0 mmol), 4,5-bis(diphenylphosphino)-9,9-dimethylxanthene (0.26 g, 0.45 mmol), palladium (II) acetate (0.067 g, 0.30 mmol) and cesium carbonate (7.33 g, 22.5 mmol) were mixed together in dioxane (50 mL) and stirred overnight at 80° C. overnight. The reaction mixture was washed with water (150 mL), and the aqueous layer was extracted with dichloromethane (3×150 mL). The combined organic layers were dried (sodium sulfate) and concentrated in vacuo. Chromatography over silica gel, eluting with hexanes/ethyl acetate, afforded the title compound as a white solid. $^1$H NMR (500 MHz, CDCl$_3$) δ 7.47 (s, 1H), 7.42 (d, J=8.3 Hz, 1H), 7.26 (t, J=7.9 Hz, 1H), 7.00 (d, J=7.6 Hz, 1H), 4.81 (d, J=3.1 Hz, 1H), 4.56-4.49 (m, 1H), 3.80-3.70 (m, 2H), 2.60-2.53 (m, 1H), 2.37 (s, 3H), 2.16-2.06 (m, 1H).

Step B: O$^2$-[(3R)-1-(3-methylphenyl)-2-oxopyrrolidin-3-yl]1-(N-tert-butylamino)diazen-1-ium-1,2-diolate The title compound was made by following the procedures described in EXAMPLE 1, substituting (3S)-3-hydroxy-1-(3-methylphenyl)pyrrolidin-2-one for tert-butyl 4-hydroxypiperidine-1-carboxylate in step A. $^1$H NMR (500 MHz, CDCl$_3$) δ 7.46 (s, 1H), 7.40 (d, J=8.3 Hz, 1H), 7.26 (t, J=7.8 Hz, 1H), 7.00 (d, J=7.6 Hz, 1H), 6.13 (s, 1H), 5.03 (t, J=7.8 Hz, 1H), 3.90 (td, J=9.2, 3.8 Hz, 1H), 3.79 (dt, J=9.7, 7.3 Hz, 1H), 2.65-2.57 (m, 1H), 2.45-2.33 (m, 4H), 1.32 (s, 9H); LC-MS: m/z 307.2 (M+H).

Example 37

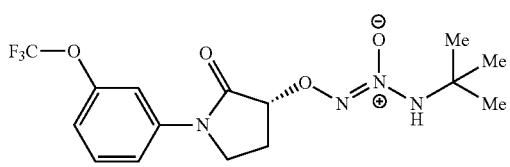 [SMILES: CC(C)(C)N/[N+]([O-])=N/O[C@@H]1CCN(c2cccc(OC(F)(F)F)c2)C1=O]

O$^2$-{(3R)-2-oxo-1-[3-(trifluoromethoxy)phenyl]pyrrolidin-3-yl}1-(N-tert-butylamino)diazen-1-ium-1,2-diolate The title compound was made by following the procedures described in EXAMPLE 36, substituting 1-bromo-3-(trifluoromethoxy)benzene for 3-bromotoluene in step A. $^1$H NMR (500 MHz, CDCl$_3$) δ 7.67 (s, 1H), 7.53 (d, J=8.4 Hz, 1H), 7.38 (t, J=8.3 Hz, 1H), 7.03 (d, J=8.3 Hz, 1H), 6.15 (s, 1H), 5.04 (t, J=7.8 Hz, 1H), 3.92 (dt, J=13.3, 4.7 Hz, 1H), 3.80 (q, J=8.2 Hz, 1H), 2.68-2.60 (m, 1H). 2.45-2.36 (m, 1H), 1.31 (s, 9H); LC-MS: m/z 399.0 (M+Na).

Example 38

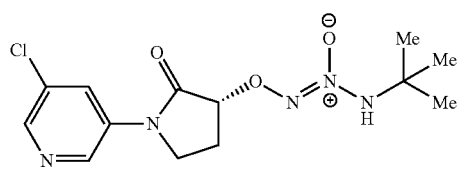 [SMILES: CC(C)(C)N/[N+]([O-])=N/O[C@@H]1CCN(c2cncc(Cl)c2)C1=O]

O$^2$-[(3R)-1-(5-chloropyridin-3-yl)-2-oxopyrrolidin-3-yl]1-(N-tert-butylamino)diazen-1-ium-1,2-diolate The title compound was made by following the procedures described in EXAMPLE 36, substituting 3-bromo-5-chloropyridine for 3-bromotoluene in step A. $^1$H NMR (500 MHz, CDCl$_3$) δ 8.64 (s, 1H), 8.39 (s, 1H), 8.35 (s, 1H), 6.17 (s, 1H), 5.06 (m, 1H), 3.98 (m, 1H), 3.85 (m, 1H), 2.70 (m, 1H), 2.47 (m, 1H), 1.32 (s, 9H); LC-MS: m/z 328.2 (M+H).

Example 39

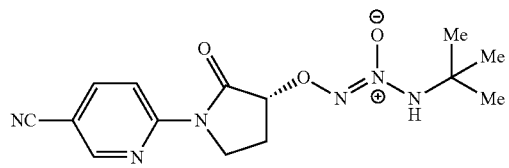 [SMILES: CC(C)(C)N/[N+]([O-])=N/O[C@@H]1CCN(c2ccc(C#N)cn2)C1=O]

O$^2$-[(3R)-1-(5-cyanopyridin-2-yl)-2-oxopyrrolidin-3-yl]1-(N-tert-butylamino)diazen-1-ium-1,2-diolate The title compound was made by following the procedures described in EXAMPLE 36, substituting 6-bromopyridine-3-carbonitrile for 3-bromotoluene in step A. $^1$H NMR (500 MHz, CDCl$_3$) δ 8.64 (d, J=2.2 Hz, 1H), 8.58 (d, J=8.8 Hz, 1H), 7.93 (dd, J=8.8, 2.3 Hz, 1H), 6.00 (s, 1H), 5.09 (t, J=8.1 Hz, 1H), 4.26 (ddd, J=11.5, 9.0, 3.6 Hz, 1H), 3.97 (dt, J=11.5, 7.7 Hz, 1H), 2.64 (dtd, J=13.6, 8.1, 3.7 Hz, 1H), 2.41 (dq, J=13.6, 8.2 Hz, 1H), 1.32 (s, 9H); LC-MS: m/z 319.1 (M+H).

Example 40

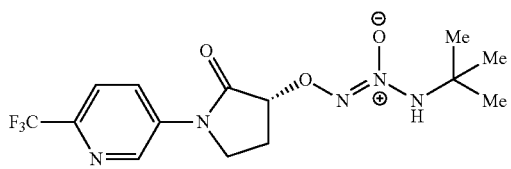 [SMILES: CC(C)(C)N/[N+]([O-])=N/O[C@@H]1CCN(c2ccc(C(F)(F)F)nc2)C1=O]

O$^2$-{(3R)-2-oxo-1-[4-(trifluoromethyl)phenyl]pyrrolidin-3-yl}1-(N-tert-butylamino)diazen-1-ium-1,2-diolate The title compound was made by following the procedures described in EXAMPLE 36, substituting 5-bromo-2-(trifluoromethyl)pyridine for 3-bromotoluene in step A. $^1$H NMR (500 MHz, CDCl$_3$) δ 8.84 (d, J=2.5 Hz, 1H), 8.48 (dd, J=8.7, 2.5 Hz, 1H), 7.70 (d, J=8.7 Hz, 1H), 5.07 (dd, J=8.4, 7.1 Hz, 1H), 4.03 (td, J=9.2, 4.0 Hz, 1H), 3.90 (dt, J=9.5, 7.3 Hz, 1H), 2.72 (dtd, J=13.8, 8.1, 4.0 Hz, 1H), 2.49 (ddt, J=13.8, 8.8, 6.9 Hz, 1H), 1.31 (s, 9H); LC-MS: m/z 362.2 (M+H).

Example 41

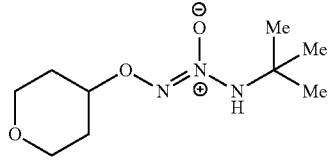 [SMILES: CC(C)(C)N/[N+]([O-])=N/OC1CCOCC1]

O$^2$-(tetrahydro-2H-pyran-4-yl)1-(N-tert-butylamino)diazen-1-ium-1,2-diolate

The title compound was made by following the procedures described in EXAMPLE 1, substituting tetrahydro-2H-pyran-4-ol for tert-butyl 4-hydroxypiperidine-1-carboxylate in step A. $^1$H NMR (500 MHz, CDCl$_3$) δ 5.85 (s, 1H), 4.41 (m, 1H), 3.98 (m, 2H), 3.52 (m, 2H), 2.05-1.80 (m, 4H), 1.31 (s, 9H); LC-MS: m/z 240.2 (M+Na).

Example 42

O$^2$-[1-(5-cyanopyridin-2-yl)piperidin-4-yl]1-(N-tert-butylamino)diazen-1-ium-1,2-diolate Step A:
6-(4-hydroxypiperidin-1-yl)pyridine-3-carbonitrile To a N,N-dimethylformamide (100 mL) solution of 2-chloro-5-cyanopyridine (36.2 g, 262 mmol) and 4-hydroxypiperidine (27.9 g, 275 mmol) was added potassium carbonate (40.1 g, 290 mmol). The reaction mixture was heated to 100° C. and stirred for 3 hours. It was cooled to room temperature, diluted with water (400 mL), and extracted with dichloromethane (3×250 mL). The combined organic extracts were washed with brine, dried (magnesium sulfate), and concentrated in vacuo to afford the title compound as a solid. This crude product was used in the subsequent step without further purification. $^1$H NMR (500 MHz, CDCl$_3$) δ 8.39 (d, J=2.3 Hz, 1H), 7.58 (dd, J=9.1, 2.4 Hz, 1H), 6.62 (d, J=9.1 Hz, 1H), 4.10 (dt, J=13.6, 5.0 Hz, 2H), 4.01 (tt, J=8.3, 3.9 Hz, 1H), 3.37 (ddd, J=13.6, 9.2, 3.4 Hz, 2H), 2.61 (s, 1H), 1.99-1.92 (m, 2H), 1.62-1.53 (m, 2H); LC-MS: m/z 204.2 (M+H).

Step B: 1-(5-cyanopyridin-2-yl)piperidin-4-yl 4-(trifluoromethyl)benzenesulfonate To a dichloromethane (50 mL) solution of 6-(4-hydroxypiperidin-1-yl)pyridine-3-carbonitrile (3.19 g, 15.7 mmol) and triethylamine (9.0 mL, 65 mmol) was added 4-(trifluoromethyl)benzenesulfonyl chloride (4.31 g, 17.6 mmol). 4-(Dimethylamino)pyridine (0.19 g, 1.6 mmol) was then added, and the reaction mixture was stirred at room temperature for 2 hours. Diethyl ether (100 mL) was added, followed by 1.0 M hydrochloric acid (70 ml, 70.0 mmol). The organic layer was separated and washed with 1.0 M hydrochloric acid (2×50 mL), saturated brine, dried (magnesium sulfate) to afford the title compound as a solid. This crude product was used in the subsequent step without further purification. $^1$H NMR (500 MHz, CDCl$_3$) δ 8.39 (d, J=2.3 Hz, 1H), 8.08 (d, J=8.3 Hz, 2H), 7.85 (d, J=8.2 Hz, 2H), 7.61 (dd, J=9.0, 2.4 Hz, 1H), 6.61 (d, J=9.1 Hz, 1H), 4.94-4.88 (m, 1H), 3.87 (ddd, J=13.7, 7.9, 3.8 Hz, 2H), 3.62 (ddd, J=13.8, 7.3, 3.9 Hz, 2H), 1.97-1.90 (m, 2H), 1.89-1.81 (m, 2H); LC-MS: m/z 412.0 (M+H).

Step C: O$^2$-[1-(5-cyanopyridin-2-yl)piperidin-4-yl]1-(N-tert-butyl-N-allylamino)diazen-1-ium-1,2-diolate To a N,N-dimethylformamide (100 mL) solution of 1-(5-cyanopyridin-2-yl)piperidin-4-yl 4-(trifluoromethyl)benzenesulfonate (5.99 g, 14.6 mmol) was added sodium (N-tert-butyl-N-allylamino)diazen-1-ium-1,2-diolate (3.51 g, 18.0 mmol). The mixture was heated to 45° C. and stirred for 2 hours. The reaction mixture was diluted with water (75 mL) and extracted with ethyl acetate (3×100 mL). The combined organic extracts were dried (magnesium sulfate), filtered and concentrated in vacuo to afford the crude product. Chromatography over silica gel, eluting with hexanes/ethyl acetate, afforded the title compound as a colorless oil that solidifies on standing. $^1$H NMR (500 MHz, CDCl$_3$) 8.39 (d, J=2.3 Hz, 1H), 7.60 (dd, J=9.0, 2.4 Hz, 1H), 6.62 (d, J=9.1 Hz, 1H), 5.78 (ddt, J=17.1, 10.1, 6.7 Hz, 1H), 5.28 (dd, J=17.1, 1.6 Hz, 1H), 5.16 (d, J=10.1 Hz, 1H), 4.62-4.55 (m, 1H), 3.99 (ddd, J=13.6, 7.2, 3.9 Hz, 2H), 3.65 (d, J=6.8 Hz, 2H), 3.51 (ddd, J=13.7, 8.2, 3.7 Hz, 2H), 2.08-2.01 (m, 2H), 1.93-1.84 (m, 2H), 1.27 (s, 9H); LC-MS: m/z 359.3 (M+H).

Step D: O$^2$-[1-(5-cyanopyridin-2-yl)piperidin-4-yl]1-(N-tert-butylamino)diazen-1-ium-1,2-diolate To a stirring methanol (150 mL) solution of O$^2$-[1-(5-cyanopyridin-2-yl)piperidin-4-yl]1-(N-tert-butyl-N-allylamino)diazen-1-ium-1,2-diolate (6.53 g, 18.2 mmol) was added sulfided platinum on carbon (5 weight %, 7.16 g, 1.84 mmol). Formic acid (1.4 mL, 37 mmol) was then added. The reaction mixture was heated to 60° C. while stirring for 2 hours, and another batch of formic acid (1.4 mL, 37 mmol) was added. After 3 hours, the reaction mixture was filtered through diatomaceous earth and concentrated in vacuo. Chromatography over silica gel, eluting with hexanes/ethyl acetate, afforded a colorless liquid. Heating this material in refluxing cyclohexane afforded the title compound as a white solid. $^1$H NMR (500 MHz, CDCl$_3$) δ 8.42 (d, J=2.3 Hz, 1H), 7.64 (dd, J=9.1, 2.3 Hz, 1H), 6.67 (d, J=9.1 Hz, 1H), 5.84 (br s, 1H), 4.52 (tt, J=7.6, 3.9 Hz, 1H), 4.04 (ddd, J=13.6, 7.4, 3.9 Hz, 2H), 3.59 (ddd, J=13.7, 8.0, 3.7 Hz, 2H), 2.10-2.03 (m, 2H), 1.98-1.90 (m, 2H), 1.32 (s, 9H); LC-MS: m/z 319.1 (M+H).

Example 43

O$^2$-[1-(5-cyanopyridin-2-yl)piperidin-4-yl]1-(N-tert-butylamino)diazen-1-ium-1,2-diolate Steps A and B: 1-(5-cyanopyridin-2-yl)piperidin-4-yl 4-(trifluoromethyl)benzenesulfonate was prepared following Steps A and B in EXAMPLE 42.

Step C: Preparation of O$^2$-[1-(5-cyanopyridin-2-yl)piperidin-4-yl]1-(N-tert-butyl-N-allylamino)diazen-1-ium-1,2-diolate To a 500 mL 3-neck round bottom, equipped with over head stirrer, thermocouple, dropping funnel, and nitrogen inlet, was charged 1-(5-cyanopyridin-2-yl)piperidin-4-yl 4-(trifluoromethyl)benzenesulfonate (30.00 g, 1 equiv), calcium bis[(1Z)-3-tert-butyl-3-(prop-2-en-1-yl)triaz-1-en-1-olate-2-oxide (17.73 g, 93 wt %, 0.60 equiv) and 2-Me-THF (180 mL, 6 vol). The resulting mixture was stirred at 55° C. for 8-17 h. 0.100 equiv of calcium bis[(1Z)-3-tert-butyl-3-(prop-2-en-1-yl)triaz-1-en-1-olate-2-oxide (2.94 g, 93 wt %) was added and the resulting mixture was stirred at 55° C. for 7-10 hours.

The reaction mixture was cooled to 25-30° C. and Solka Flock powdered cellulose (30 g, 100 wt %) was added. The resulting slurry was stirred at room temperature for 10 min and was filtered through Solka Flock powdered cellulose (15 g, 50 wt %), rinsed with 2-methyl-THF (180 mL, 6 vol). Assay desired product O$^2$-[1-(5-cyanopyridin-2-yl)piperidin-4-yl]1-(N-tert-butyl-N-allylamino)diazen-1-ium-1,2-diolate in the combined filtrates was 25.1 g. The reaction mixture was concentrated to 60 mL (2 vol, total volume) at 30-35° C. The resulting solution was cooled to 20° C. and seeded (50 mg of seed). Slurry was formed and the resulting slurry was stirred at 20° C. for 0.5 h. Heptanes (90 mL, 3 vol) was added dropwise over 0.5 h. The resulting slurry was stirred at 20° C. for 1 h, and at 10° C. for 1 h.

The crystalline product $O^2$-[1-(5-cyanopyridin-2-yl)piperidin-4-yl]1-(N-tert-butyl-N-allylamino)diazen-1-ium-1,2-diolate was collected by filtration, rinsed with heptanes:2-Me-THF (3:1, 45 mL, 1.5 vol). The wet cake was slurry washed with D.I. water (60 mL×1, 2 vol) and dried with D.I. water (30 mL×1, 1 vol) and dried under vacuum with nitrogen sweep to give dry product $O^2$-[1-(5-cyanopyridin-2-yl)piperidin-4-yl]1-(N-tert-butyl-N-allylamino)diazen-1-ium-1,2-diolate (23.76 g) as off white crystalline solid, m.p. 92.0-92.8° C. $^1$H NMR (500 MHz, $CDCl_3$) δ: 8.39 (d, J=2.4 Hz, 1H), 7.59 (dd, J=8.9, 2.4 Hz, 1H), 6.61 (d, J=8.9 Hz, 1H), 5.78 (ddt, J=17.1, 10.2, 6.7 Hz, 1H), 5.27 (ddd, J=17.1, 2.6, 1.4 Hz, 1H), 5.15 (ddd, J=10.2, 2.6, 1.1 Hz, 1H), 4.58 (m, 1H), 3.98 (ddd, J=13.4, 7.2, 3.9 Hz, 2H), 3.64 (dt, J=6.7, 1.1 Hz, 2H), 3.51 (ddd, J=13.4, 8.1, 3.7 Hz, 2H), 2.05 (m, 2H), 1.89 (m, 2H), 1.26 (s, 9H).

Step D: Preparation of $O^2$-[1-(5-cyanopyridin-2-yl)piperidin-4-yl]1-(N-tert-butylamino)diazen-1-ium-1,2-diolate To a nitrogen purged 250 mL 3-neck round bottom, equipped with overhead stirrer, thermocouple, and nitrogen inlet was charged $O^2$-[1-(5-cyanopyridin-2-yl)piperidin-4-yl]1-(N-tert-butyl-N-allylamino)diazen-1-ium-1,2-diolate (10.0 g) and sodium borohydride (1.306 g). The flask was purged with nitrogen for 1 h. Degassed ethanol (45 mL) was added and the slurry stirred slowly at 20-22° C.

In a separate 10 mL round bottom flask under nitrogen atmosphere was charged palladium acetate (62 mg) and DPPP (148 mg). The flask was purged with nitrogen for 30 min and degassed ethanol (6.6 mL) added at room temperature. The mixture was stirred for 30 min at room temperature to obtain a yellow homogeneous solution.

The yellow catalyst solution was added, via syringe, to the allyl $O^2$-[1-(5-cyanopyridin-2-yl)piperidin-4-yl]1-(N-tert-butylamino)diazen-1-ium-1,2-diolate slurry above in one portion. The yellow slurry was aged at 25° C. for 1 hour and then warmed to 40° C. for 4 h. Reaction progress was monitored by HPLC. Reaction was >99.9% complete in 3.5 h at 40 C.

On complete reaction the mixture was cooled to 25° C. and seeded with crystalline $O^2$-[1-(5-cyanopyridin-2-yl)piperidin-4-yl]1-(N-tert-butylamino)diazen-1-ium-1,2-diolate (5 mg). The mixture was aged at 20° C. for 30 min to give a thick, but stirrable slurry. The slurry was cooled to 5° C. and a solution of acetic acid (4.98 g) in water (100 mL) added over 30 min maintaining 5-10° C.

The slurry was aged at 5-10° C. for 30 min. Tan solids were filtered and washed with 2:1 water/ethanol (20 mL) and air dried (on funnel) for 3 hours. Crude yield was 12.6 g (with water content approx 30% w/w)

Tan solid was dissolved in IPAC (120 mL) at room temperature. $SiO^2$ (4 g) was added and the slurry stirred for 30 min at room temperature. The slurry was filtered through $SiO^2$ (4 g) over 10 min and the cake washed with IPAC (40 mL). Combined filtrates were assayed. Assay yield at this point was 52.0 mg/mL (161 mL), 8.38 g.

The IPAC solution was recharged to the vessel through an in-line 5 μm filter clarification and concentrated to about 50 mL. The batch was seeded with $O^2$-[1-(5-cyanopyridin-2-yl)piperidin-4-yl]1-(N-tert-butylamino)diazen-1-ium-1,2-diolate (5 mg) and allowed to stir for 30 min to give slurry. Heptane (50 mL) was added and the slurry solvent switched to >90% heptane at constant volume and 30-40° C. The resultant slurry (IPAC level at 5-10% v/v by HPLC assay) was aged at 20° C. for 30 min. The slurry was filtered and washed with heptane (30 mL), dried in air 1 h and in vacuo at 30° C. overnight to obtain 8.1 g (>99.7A % 210 nm).

Activity

Compounds of the invention were evaluated for blood pressure reduction efficacy using the following canine telemetry protocol described below.

Male beagle dogs (approximately 1-3 years old) with a body weight of between 10 and 16 kg were surgically implanted with DSI radiotelemetry devices (model: TL11M2-D70-PCT). Briefly, under an inhalant anesthesia, isoflurane/oxygen mixture (1-3.5%/to effect), the body of the telemetry device was positioned and secured intra-abdominally. Subsequently, the arterial catheter of the telemetry device was passed subcutaneously to the inguinal area and introduced into the femoral artery and advanced to the level of the descending aorta. The catheter was secured with 2-0 silk ligatures. The muscle and underlying fascia was closed over the catheter using absorbable suture and the skin was closed using non-absorbable suture. The animals were allowed a minimum recovery period of 2 weeks between surgery and the evaluation of test compounds.

Compound evaluation consisted of a 3 day paradigm at a 3 mg/kg dose. On the first day, no compounds were administered during a 24 hour period of baseline data collection. Blood pressure and heart rate data were collected continuously for one minute periods at 10 minute intervals. On the days of compound administration half the animals received test article with the other half receiving the vehicle used for compound formulation. All test materials were administered by oral gavage in a volume of 1 mL/kg. Data are expressed either as raw values (mm Hg or beats per minute) or as the change from baseline (average value for about 12 hours in low activity period prior to dosing). Change is SBP (systolic blood pressure) and PP (pulse pressure) over time is shown below:

| Example | ΔSBP (mm Hg) | | | ΔPP (mm Hg) | | |
|---|---|---|---|---|---|---|
| | 1-6 h | 6-12 h | 12-18 h | 1-6 h | 6-12 h | 12-18 h |
| 9 | −24 | −25 | −18 | −23 | −27 | −11 |
| 22 | −19 | −18 | −21 | −15 | −17 | −16 |
| 32 | −10 | −17 | −17 | −7 | −12 | −13 |
| 36 | −23 | −17 | −14 | −9 | −7 | −4 |

The exemplified compounds reduced blood pressure over the indicated time periods.

What is claimed is:
1. A compound of formula I:

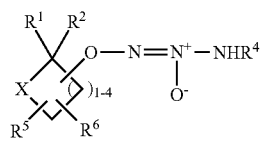

or a pharmaceutically acceptable salt thereof, wherein X is O or $NR^7$;

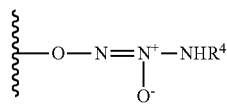

is attached to any ring carbon atom other than the carbon to which $R^1$ and $R^2$ are attached;

$R^1$ is hydrogen, —C(O)O$C_{1-6}$alkyl, or —C(O)OH, or together with $R^2$, forms =O;

$R^2$ is hydrogen, or together with $R^1$, forms =O;

$R^4$ is
- —$C_{1-6}$alkyl,
- —$CD_2C_{1-5}$alkyl,
- —$C_{2-5}$alkylene-OH,
- —$C_{2-5}$alkylene-O—C(O)$C_{1-6}$alkyl,
- —$C_{1-6}$alkylene-aryl, or
- —$CH_2CH=CH_2$;

$R^5$ and $R^6$, which are attached to any available carbon ring atom, are independently
- hydrogen,
- deuterium,
- —$C_{1-6}$alkyl,
- —C(O)O$C_{1-6}$alkyl,
- —C(O)OH,
- aryl,
- or $R^5$ and $R^6$, when they are attached to the same carbon atom, together form =O;

$R^7$ is
- hydrogen,
- —$C_{1-6}$alkyl,
- —$C_{1-6}$alkylene-aryl,
- —$C_{1-6}$alkyleneC(O)O—$C_{1-6}$alkyl,
- —$C_{1-6}$alkylene-$CR^8R^9R^{10}$,
- —CN,
- —C(O)O—$C_{1-6}$alkyl,
- —C(O)O—$C_{1-6}$alkylene $CR^8R^9R^{10}$,
- —C(O)$C_{1-6}$alkyl,
- —C(O)O$C_{3-6}$carbocycle,
- —C(O)$CHF_2$,
- —C(O)$CF_3$,
- —C(O)$CH_2$OH,
- —C(O)aryl,
- —C(O)heteroaryl, wherein heteroaryl is an unsaturated 5- or 6-membered ring containing 1-4 heteroatoms selected from N, O and S,
- —C(O)$C_{1-6}$alkyleneOH,
- —C(O)$C_{3-6}$carbocycle,
- —C(O)$NH_2$,
- —C(O)NH$C_{1-6}$alkyl,
- —C(O)NH-adamantyl,
- —C(O)heterocycle, wherein heterocycle is a saturated monocyclic 5- to 8-membered ring containing 1-4 heteroatoms selected from N, O and S, or a 7- to 12-membered saturated bicyclic ring system containing 1-6 heteroatoms selected from N, O and S,
- —C(O)NH$C_{3-6}$carbocycle,
- —C(O)N($C_{1-6}$alkyl)Cl$_{1-6}$alkyl,
- —C(O)NHSO$_2$aryl,
- —SO$C_{1-6}$alkyl,
- —SO$_2C_{1-6}$alkyl,
- —SO$_2$NH($C_{1-6}$alkyl),
- —SO$_2$N($C_{1-6}$alkyl)($C_{1-6}$alkyl),
- —SO$_2CF_3$,
- —SO$_2$aryl,
- —SO$_2$heteroaryl, wherein heteroaryl is an unsaturated 5- or 6-membered ring containing 1-4 heteroatoms selected from N, O and S,
- aryl,
- an unsaturated 5- or 6-membered heteroaryl ring containing 1-4 heteroatoms selected from N, O and S, or
- —$C_{3-6}$carbocycle;

wherein aryl, alkyl, alkylene, carbocycle, heteroaryl, and heterocycle are unsubstituted or substituted with 1-4 groups independently selected from —CN, halogen, —$CF_3$, —$OCF_3$, —C(O)$NH_2$, —$C_{1-6}$alkyl, —$C_{3-6}$carbocycle, =O, —C(O)O$C_{1-6}$alkyl,
- —COOH, —C($CH_3$)$_2$OH,
- —SO$_2$($C_{1-6}$alkyl), aryl, an unsaturated 5-membered heteroaryl ring containing 1-3 nitrogen atoms, or
- —O$C_{1-6}$alkyl, wherein $R^8$ and $R^9$, together with the carbon to which they are attached, form a $C_{3-6}$carbocycle or 4-8-membered heterocycle, and wherein $R^{10}$ is $C_{1-6}$alkyl.

2. A compound of claim 1, of formula

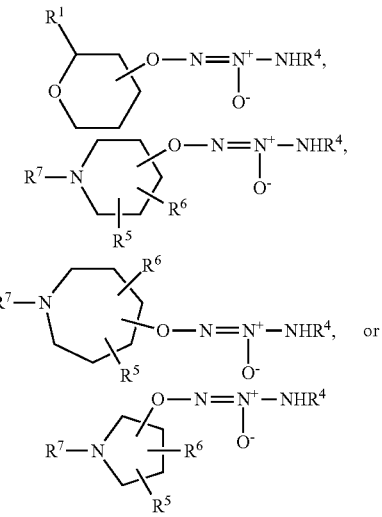

or a pharmaceutically acceptable salt thereof.

3. A compound of claim 1, of formula

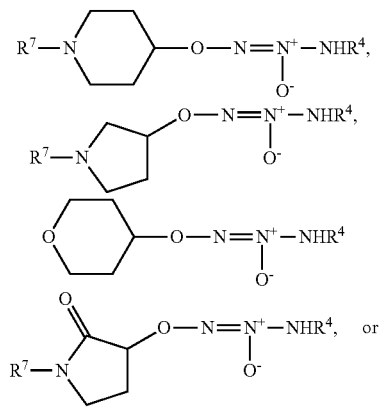

-continued

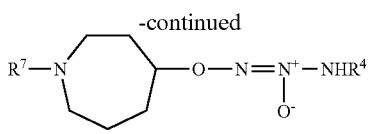

or a pharmaceutically acceptable salt thereof.

4. A compound of claim 1, of formula

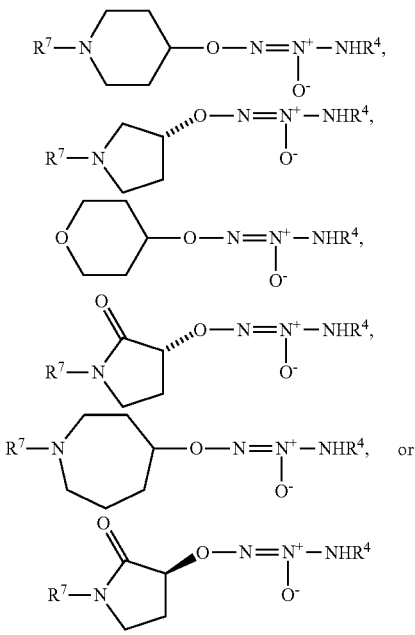

or a pharmaceutically acceptable salt thereof.

5. A compound of claim 1, wherein X is —NR$^7$ and R$^7$ is
 —C$_{1-6}$alkyl,
 —C$_{1-6}$alkylene-CR$^8$R$^9$R$^{10}$,
 —C(O)O—C$_{1-6}$alkyl,
 —C(O)O—C$_{1-6}$alkylene CR$^8$R$^9$R$^{10}$,
 —C(O)C$_{1-6}$alkyl,
 —C(O)OC$_{3-6}$carbocycle,
 —C(O)CF$_3$,
 —C(O)aryl,
 —C(O)heteroaryl, wherein heteroaryl is an unsaturated 6-membered ring containing 1-2 nitrogen atoms,
 —C(O)NHC$_{1-6}$alkyl,
 —C(O)NH-adamantyl,
 —SO$_2$C$_{1-6}$alkyl,
 aryl, or
 heteroaryl, wherein heteroaryl is an unsaturated 6-membered ring containing 1-2 nitrogen atoms,
wherein aryl, alkyl, alkylene, carbocycle, and heteroaryl are unsubstituted or substituted with 1-4 groups independently selected from —CN, —CF$_3$, Cl, —OCF$_3$, —C(O)NH$_2$, —C$_{1-6}$alkyl, —C$_{3-6}$carbocycle, =O, —C(O)OC$_{1-6}$alkyl, aryl, an unsaturated 5-membered heteroaryl ring containing 3 nitrogen atoms or —OC$_{1-6}$alkyl,
wherein R$^8$ and R$^9$, together with the carbon to which they are attached, form a C$_{3-6}$carbocycle or 4-8-membered heterocycle, and
wherein R$^{10}$ is C$_{1-6}$alkyl,
or a pharmaceutically acceptable salt thereof.

6. A compound of claim 5, wherein R$^7$ is —C$_{1-6}$alkyl, wherein alkyl is unsubstituted or substituted with 1 or 2-CF$_3$, or a pharmaceutically acceptable salt thereof.

7. A compound of claim 5, wherein
R$^7$ is —C(O)O—C$_{1-6}$alkyl, —C(O)C$_{1-6}$alkyl, —C(O)O—C$_{1-6}$alkylene CR$^8$R$^9$R$^{10}$, —C(O)OC$_{3-6}$carbocycle, —C(O)CF$_3$, —C(O)aryl, —C(O)pyridyl, —C(O)NHC$_{1-6}$alkyl, or —C(O)NH-adamantyl,
wherein alkyl is unsubstituted or substituted with aryl or —CF$_3$,
wherein R$^8$ and R$^9$, together with the carbon to which they are attached, form a C$_{3-6}$carbocycle or 4-8-membered heterocycle, and
wherein R$^{10}$ is C$_{1-6}$alkyl,
or a pharmaceutically acceptable salt thereof.

8. A compound of claim 5, wherein R$^7$ is —SO$_2$C$_{1-6}$alkyl, or a pharmaceutically acceptable salt thereof.

9. A compound of claim 5, wherein R$^7$ is aryl, wherein aryl is unsubstituted or substituted with 1-2 groups independently selected from —CN, —CF$_3$, —OCF$_3$, —CH$_3$ or an unsaturated 5-membered heteroaryl ring having 3 nitrogen atoms,
or a pharmaceutically acceptable salt thereof.

10. A compound of claim 5, wherein R$^7$ is an unsaturated heteroaryl 6-membered ring containing 1-2 nitrogen atoms, wherein heteroaryl is unsubstituted or substituted with 1-4 groups independently selected from Cl, an unsaturated 5-membered heteroaryl ring containing 3 nitrogen atoms, —CN, —CF$_3$, and —C(O)NH$_2$, or a pharmaceutically acceptable salt thereof.

11. A compound of claim 10, or a pharmaceutically acceptable salt thereof, wherein R$^7$ is

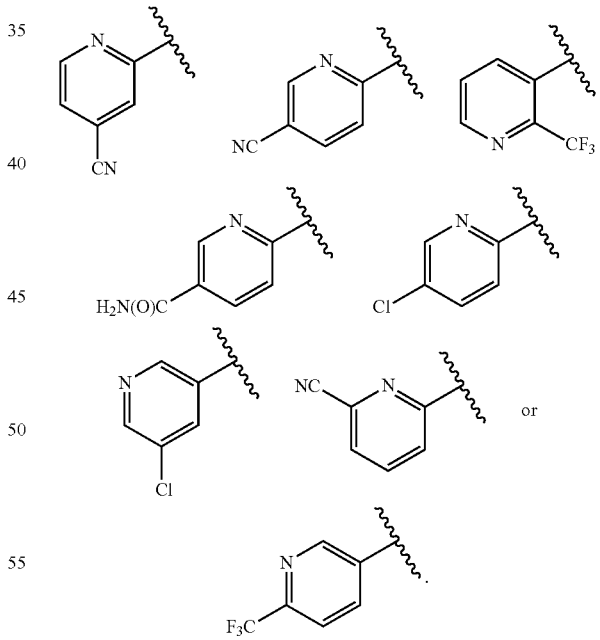

12. A compound of claim 1, or a pharmaceutically acceptable salt thereof, wherein R$^1$, R$^2$, R$^5$ and R$^6$ are hydrogen.

13. A compound of claim 1, or a pharmaceutically acceptable salt thereof, wherein R$^1$ and R$^2$, together with the atom to which they are attached, form =O, and R$^5$ and R$^6$ are hydrogen.

14. A compound of claim 1, or a pharmaceutically acceptable salt thereof, wherein R$^4$ is —C$_{1-6}$alkyl.

15. A compound of claim 14, or a pharmaceutically acceptable salt thereof, wherein $R^4$ is —C(CH$_3$)$_3$.

16. A compound of claim 1, or a pharmaceutically acceptable salt thereof, wherein X is —NR$^7$ and R$^7$ is
- —C$_{1-6}$alkyl,
- —C$_{1-6}$alkylene-aryl,
- —C$_{1-6}$alkyleneC(O)O—C$_{1-6}$alkyl,
- —C$_{1-6}$alkylene-CR$^8$R$^9$R$^{10}$,
- —CN,
- —C(O)O—C$_{1-6}$alkyl,
- —C(O)O—C$_{1-6}$alkylene CR$^8$R$^9$R$^{10}$,
- —C(O)C$_{1-6}$alkyl,
- —C(O)OC$_{3-6}$-carbocycle,
- —C(O)CHF$_2$,
- —C(O)CF$_3$,
- —C(O)CH$_2$OH,
- —C(O)aryl,
- —C(O)heteroaryl, wherein heteroaryl is an unsaturated 5- or 6-membered ring containing 1-4 heteroatoms selected from N, O and S,
- —C(O)C$_{1-6}$alkyleneOH,
- —C(O)C$_{3-6}$-carbocycle,
- —C(O)NH$_2$,
- —C(O)NHC$_{1-6}$alkyl,
- —C(O)NH-adamantyl,
- —C(O)heterocycle, wherein heterocycle is a saturated monocyclic 5- to 8-membered ring containing 1-4 heteroatoms selected from N, O and S, or a 7- to 12-membered saturated bicyclic ring system containing 1-6 heteroatoms selected from N, O and S,
- —C(O)NHC$_{3-6}$carbocycle,
- —C(O)N(C$_{1-6}$alkyl)C$_{1-6}$alkyl,
- —C(O)NHSO$_2$aryl,
- —SOC$_{1-6}$alkyl,
- —SO$_2$C$_{1-6}$alkyl,
- —SO$_2$NH(C$_{1-6}$alkyl),
- —SO$_2$N(C$_{1-6}$alkyl)(C$_{1-6}$alkyl),
- —SO$_2$CF$_3$,
- —SO$_2$aryl,
- —SO$_2$heteroaryl, wherein heteroaryl is an unsaturated 5- or 6-membered ring containing 1-4 heteroatoms selected from N, O and S,
- aryl,
- an unsaturated 5- or 6-membered heteroaryl ring containing 1-4 heteroatoms selected from N, O and S, or
- —C$_{3-6}$carbocycle;
- wherein aryl, alkyl, alkylene, carbocycle, heteroaryl, and heterocycle are unsubstituted or substituted with 1-4 groups independently selected from —CN, halogen, —CF$_3$, —OCF$_3$, —C(O)NH$_2$, —C$_{1-6}$alkyl, —C$_{3-6}$carbocycle, =O, —C(O)OC$_{1-6}$alkyl, —COOH, —C(CH$_3$)$_2$OH, —SO$_2$(C$_{1-6}$alkyl), aryl, an unsaturated 5-membered heteroaryl ring containing 1-3 nitrogen atoms, or —OC$_{1-6}$alkyl,
- wherein R$^8$ and R$^9$, together with the carbon to which they are attached, form a C$_{3-6}$carbocycle or 4-8-membered heterocycle, and
- wherein R$^{10}$ is C$_{1-6}$alkyl.

17. A compound of claim 1, which is
- O$^2$-[1-(tert-butoxycarbonyl)piperidin-4-yl]1-(N-tert-butylamino)diazen-1-ium-1,2-diolate,
- O$^2$-[(3R)-1-(tert-butoxycarbonyl)pyrrolidin-3-yl]1-(N-tert-butylamino)diazen-1-ium-1,2-diolate,
- O$^2$-{(3R)-1-[(cyclohexyloxy)carbonyl]pyrrolidin-3-yl}1-(N-tert-butylamino)diazen-1-ium-1,2-dioate,
- O$^2$-{(3R)-1-[(propan-2-yloxy)carbonyl]pyrrolidin-3-yl}1-(N-tert-butylamino)diazen-1-ium-1,2-diolate,
- O$^2$-{(3R)-1-[(2,2-dimethylpropoxy)carbonyl]pyrrolidin-3-yl}1-(N-tert-butylamino)diazen-1-ium-1,2diolate,
- O$^2$-{(3R)-1-[(cyclopropylmethoxy)carbonyl]pyrrolidin-3-yl}1-(N-tert-butylamino)diazen-1-ium-1,2diolate,
- O$^2$-[(3R)-1-{[(3-methyloxetan-3-yl)methoxy]carbonyl}pyrrolidin-3-yl]1-(N-tert-butylamino)diazen-1-ium-1,2-diolate,
- O$^2$-[(3R)-1-(2,2,2-trifluoroethyl)pyrrolidin-3-yl]1-(N-tert-butylamino)diazen-1-ium-1,2-diolate,
- O$^2$-[(3R)-1-(tert-butylcarbamoyl)pyrrolidin-3-yl]1-(N-tert-butylamino)diazen-1-ium-1,2-diolate,
- O$^2$-[(3R)-1-(tricyclo[3.3.1.13,7]dec-1-ylcarbamoyl)pyrrolidin-3-yl]1-(N-tert-butylamino)diazen-1-ium-1,2-diolate,
- O$^2$-{(3R)-1-[(2-phenylpropan-2-yl)carbamoyl]pyrrolidin-3-yl}1-(N-tert-butylamino)diazen-1-ium-1,2-diolate,
- O$^2$-{(3R)-1-[(1,1,1-trifluoro-2-methylpropan-2-yl)carbamoyl]pyrrolidin-3-yl}1-(N-tert-butylamino)diazen-1-ium-1,2-diolate,
- (±)—O$^2$-[1-(tert-butylcarbamoyl)azepan-4-yl]1-(N-tert-butylamino)diazen-1-ium-1,2-diolate,
- O$^2$-(1-acetylpiperidin-4-yl)1-(N-tert-butylamino)diazen-1-ium-1,2-diolate,
- O$^2$-[1-(2,2-dimethylpropanoyl)piperidin-4-yl]1-(N-tert-butylamino)diazen-1-ium-1,2-diolate,
- O$^2$-{1-[(4-cyanophenyl)carbonyl]piperidin-4-yl}1-(N-tert-butylamino)diazen-1-ium-1,2-diolate,
- O$^2$-{1-[(2-methylphenyl)carbonyl]piperidin-4-yl}1-(N-tert-butylamino)diazen-1-ium-1,2-diolate,
- (±)—O$^2$-[1-(pyridin-4-ylcarbonyl)azepan-4-yl]1-(N-tert-butylamino)diazen-1-ium-1,2-diolate,
- O$^2$-[(3R)-1-(methylsulfonyl)pyrrolidin-3-yl]1-(N-tert-butylamino)diazen-1-ium-1,2-diolate,
- O$^2$-[1-(methylsulfonyl)piperidin-4-yl]1-(N-tert-butylamino)diazen-1-ium-1,2-diolate,
- O$^2$-[1-(tert-butylsulfonyl)piperidin-4-yl]1-(N-tert-butylamino)diazen-1-ium-1,2-diolate,
- O$^2$-[1-(5-cyanopyridin-2-yl)piperidin-4-yl]1-(N-tert-butylamino)diazen-1-ium-1,2-diolate,
- O$^2$-[1-(4-cyanopyridin-2-yl)piperidin-4-yl]1-(N-tert-butylamino)diazen-1-ium-1,2-diolate,
- O$^2$-[1-(3-cyanophenyl)piperidin-4-yl]1-(N-tert-butylamino)diazen-1-ium-1,2-diolate,
- O$^2$-[(3R)-1-(5-cyanopyrazin-2-yl)pyrrolidin-3-yl]1-(N-tert-butylamino)diazen-1-ium-1,2-diolate,
- O$^2$-[(3R)-1-(3-cyanophenyl)pyrrolidin-3-yl]1-(N-tert-butylamino)diazen-1-ium-1,2-diolate,
- O$^2$-{(3R)-1-[2-(trifluoromethyl)pyridin-3-yl]pyrrolidin-3-yl}1-(N-tert-butylamino)diazen-1-ium-1,2-diolate,
- O$^2$-[(3R)-1-(6-cyanopyridin-2-yl)pyrrolidin-3-yl]1-(N-tert-butylamino)diazen-1-ium-1,2-diolate,
- O$^2$-{(3R)-1-[3-(trifluoromethyl)phenyl]pyrrolidin-3-yl}1-(N-tert-butylamino)diazen-1-ium-1,2-diolate,
- O$^2$-[1-(5-chloropyridin-2-yl)piperidin-4-yl]1-(N-tert-butylamino)diazen-1-ium-1,2-diolate,
- O$^2$-[1-(5-carbamoylpyridin-2-yl)piperidin-4-yl]1-(N-tert-butylamino)diazen-1-ium-1,2-diolate,
- O$^2$-{(3R)-1-[3-(1H-1,2,3-triazol-1-yl)phenyl]pyrrolidin-3-yl}1-(N-tert-butylamino)diazen-1-ium-1,2-diolate,
- O$^2$-{1-[3-(1H-1,2,4-triazol-1-yl)phenyl]piperidin-4-yl}1-(N-tert-butylamino)diazen-1-ium-1,2-diolate,
- O$^2$-{1-[3-(1H-1,2,3-triazol-1-yl)phenyl]piperidin-4-yl}1-(N-tert-butylamino)diazen-1-ium-1,2-diolate, O²-{1-[5-(1H-1,2,3-triazol-1-yl)pyridin-2-yl]piperidin-4-yl}1-(N-tert-butylamino)diazen-1-ium-1,2-diolate, O²-(tetrahydro-2H-pyran-4-yl)1-(N-tert-butylamino)diazen-1-ium-1,2-diolate, O²-[(3R)-1-(3-methylphenyl)-2-oxopyrrolidin-3-yl]1-(N-tert-butylamino)diazen-1-ium-1,2-diolate, O²-{(3R)-2-oxo-1-[3-(trifluoromethoxy)phenyl]pyrrolidin-3-yl}1-(N-tert-butylamino)diazen-1-ium-1,2-diolate, O²-[(3R)-1-(5-chloropyridin-3-yl)-2-oxopyrrolidin-3-yl]1-(N-tert-butylamino)diazen-1-ium-1,2-diolate, O²-[(3R)-1-(5-cyanopyridin-2-yl)-2-oxopyrrolidin-3-yl]1-(N-tert-butylamino)diazen-1-ium-1,2-diolate, or O²-{(3R)-2-oxo-1-[4-(trifluoromethyl)phenyl]pyrrolidin-3-yl}1-(N-tert-butylamino)diazen-1-ium-1,2-diolate, or a pharmaceutically acceptable salt thereof.

18. A compound of claim 17, which is
O²-[1-(5-cyanopyridin-2-yl)piperidin-4-yl]1-(N-tert-butylamino)diazen-1-ium-1,2-diolate,
O²-[1-(4-cyanopyridin-2-yl)piperidin-4-yl]1-(N-tert-butylamino)diazen-1-ium-1,2-diolate,
O²-{(3R)-1-[2-(trifluoromethyl)pyridin-3-yl]pyrrolidin-3-yl}1-(N-tert-butylamino)diazen-1-ium-1,2-diolate,
O²-[(3R)-1-(6-cyanopyridin-2-yl)pyrrolidin-3-yl]1-(N-tert-butylamino)diazen-1-ium-1,2-diolate,
O²-[1-(5-chloropyridin-2-yl)piperidin-4-yl]1-(N-tert-butylamino)diazen-1-ium-1,2-diolate,
O²-[1-(5-carbamoylpyridin-2-yl)piperidin-4-yl]1-(N-tert-butylamino)diazen-1-ium-1,2-diolate,
O²-[(3R)-1-(5-chloropyridin-3-yl)-2-oxopyrrolidin-3-yl]1-(N-tert-butylamino)diazen-1-ium-1,2-diolate,
O²-[(3R)-1-(5-cyanopyridin-2-yl)-2-oxopyrrolidin-3-yl]1-(N-tert-butylamino)diazen-1-ium-1,2-diolate,
O²-{(3R)-2-oxo-1-[4-(trifluoromethyl)phenyl]pyrrolidin-3-yl}1-(N-tert-butylamino)diazen-1-ium-1,2-diolate,
or pharmaceutically acceptable salt thereof.

19. A pharmaceutical composition comprising a compound of claim 1 and a pharmaceutically acceptable carrier.

20. A pharmaceutical composition comprising a compound of claim 17 and a pharmaceutically acceptable carrier.

21. A pharmaceutical composition comprising a compound of claim 17, a diuretic, and a pharmaceutically acceptable carrier.

22. A pharmaceutical composition comprising a compound of claim 17, an angiotensin II receptor antagonist, and a pharmaceutically acceptable carrier.

23. A method for treating hypertension in a patient which comprises administering to the patient a therapeutically effective amount of the composition of claim 20.

24. A compound of claim 18, or a pharmaceutically acceptable salt thereof, which is O²-[1-(5-cyanopyridin-2-yl)piperidin-4-yl]1-(N-tert-butylamino)diazen-1-ium-1,2-diolate.

25. A compound of claim 18, or a pharmaceutically acceptable salt thereof, which is O²-[1-(4-cyanopyridin-2-yl)piperidin-4-yl]1-(N-tert-butylamino)diazen-1-ium-1,2-diolate.

26. A compound of claim 18, or a pharmaceutically acceptable salt thereof, which is O²-{(3R)-1-[2-(trifluoromethyl)pyridin-3-yl]pyrrolidin-3-yl}1-(N-tert-butylamino)diazen-1-ium-1,2-diolate.

27. A compound of claim 18, or a pharmaceutically acceptable salt thereof, which is O²-[(3R)-1-(6-cyanopyridin-2-yl)pyrrolidin-3-yl]1-(N-tert-butylamino)diazen-1-ium-1,2-diolate.

28. A compound of claim 18, or a pharmaceutically acceptable salt thereof, which is O²-[1-(5-chloropyridin-2-yl)piperidin-4-yl]1-(N-tert-butylamino)diazen-1-ium-1,2-diolate.

29. A compound of claim 18, or a pharmaceutically acceptable salt thereof, which is O²-[1-(5-carbamoylpyridin-2-yl)piperidin-4-yl]1-(N-tert-butylamino)diazen-1-ium-1,2-diolate.

30. A compound of claim 18, or a pharmaceutically acceptable salt thereof, which is O²-[(3R)-1-(5-chloropyridin-3-yl)-2-oxopyrrolidin-3-yl]1-(N-tert-butylamino)diazen-1-ium-1,2-diolate.

31. A compound of claim 18, or a pharmaceutically acceptable salt thereof, which is O²-[(3R)-1-(5-cyanopyridin-2-yl)-2-oxopyrrolidin-3-yl]1-(N-tert-butylamino)diazen-1-ium-1,2-diolate.

32. A compound of claim 18, or a pharmaceutically acceptable salt thereof, which is O²-{(3R)-2-oxo-1-[4-(trifluoromethyl)phenyl]pyrrolidin-3-yl}1-(N-tert-butylamino)diazen-1-ium-1,2-diolate.

* * * * *